(12) United States Patent
Baura

(10) Patent No.: US 6,471,655 B1
(45) Date of Patent: Oct. 29, 2002

(54) METHOD AND APPARATUS FOR THE NONINVASIVE DETERMINATION OF ARTERIAL BLOOD PRESSURE

(75) Inventor: Gail D. Baura, San Diego, CA (US)

(73) Assignee: VitalWave Corporation, San Diego, CA (US)

( * ) Notice: Subject to any disclaimer, the term of this patent is extended or adjusted under 35 U.S.C. 154(b) by 0 days.

(21) Appl. No.: 09/342,549

(22) Filed: Jun. 29, 1999

(51) Int. Cl.[7] .................................................. A61B 5/00
(52) U.S. Cl. ........................................ 600/485; 600/500
(58) Field of Search ............................... 600/481, 485, 600/490, 493–496, 500, 504

(56) References Cited

U.S. PATENT DOCUMENTS

| | | |
|---|---|---|
| 3,527,197 A | 9/1970 | Ware et al. |
| 3,601,120 A | 8/1971 | Massie et al. |

(List continued on next page.)

FOREIGN PATENT DOCUMENTS

| | | |
|---|---|---|
| DE | 42 18 319 A | 12/1993 |
| EP | 342 249 A1 | 5/1988 |
| EP | 0 299 827 | 1/1989 |
| EP | 0595 666 B1 | 9/1993 |
| EP | 0 603 666 A3 | 12/1993 |
| EP | 0818176 A | 1/1998 |
| WO | WO 92/07508 | 10/1991 |
| WO | 95/00074 | 1/1995 |
| WO | WO 98 25511 A | 6/1998 |
| WO | 00/03635 | 7/1999 |

OTHER PUBLICATIONS

U.S. patent application Ser. No. 09/120,069 filed Jul. 20, 1998 entitled Apparatus and Method for Non–Invasively Monitoring a Subject's Arterial Blood Pressure.

Cariou, Alain, et al. (1998) "Noninvasive Cardiac Output Monitoring by Aortic Blood Flow Determination: Evaluation of the Sometec Cynemo–3000 System," Critical Care Medicine, vol. 26, No. 12, pp. 2066–2072.

Advertisement for HemoSonic™ 100 by Arrow International—licensed under U.S. Patent 5,479,928 listed above.

Mehra, Mandeep R., et al. (May/Jun. 2000) "Emergence of Electronic Home Monitoring in Chronic Heart Failure: Rationale, Feasibility, and Early Results with the HomMed Sentry–Observer System," (consisting of 3 pages).

Drzewiecki, G. (1995) "Noninvasive Assessment of Arterial Blood Pressure and Mechanics", The Biomedical Engineering Handbook CRC Press, Boca Raton, Fl, pp. 1196–1211.

(List continued on next page.)

Primary Examiner—Robert L. Nasser
(74) Attorney, Agent, or Firm—Gazdzinski & Associates

(57) ABSTRACT

A method and apparatus for determining the mean arterial blood pressure (MAP) of a subject during tonometric conditions. In one embodiment, the apparatus comprises one or more pressure and ultrasound transducers placed over the radial artery of a human subject's wrist, the latter transmitting and receiving acoustic energy so as to permit the measurement of blood velocity during periods of variable compression of the artery. During compression, the ultrasound velocity waveforms are recorded and processed using time-frequency analysis. The time at which the mean time-frequency distribution is maximal corresponds to the time at which the transmural pressure equals zero, and the mean pressure read by the transducer equals the mean pressure within the artery. In another aspect of the invention, the ultrasound transducer is used to position the transducer over the artery such that the accuracy of the measurement is maximized. In yet another aspect of the invention, a wrist brace useful for measuring blood pressure using the aforementioned apparatus is disclosed.

26 Claims, 15 Drawing Sheets

U.S. PATENT DOCUMENTS

| | | | |
|---|---|---|---|
| 3,617,993 A | 11/1971 | Massie et al. | |
| 3,663,932 A | 5/1972 | Mount et al. | |
| 3,791,378 A | 2/1974 | Hochbert et al. | |
| 3,885,551 A | 5/1975 | Massie | |
| 4,109,647 A | 8/1978 | Stern et al. | |
| 4,127,114 A | 11/1978 | Bretscher | |
| 4,154,231 A | 5/1979 | Russell | |
| 4,239,047 A | 12/1980 | Griggs, III et al. | |
| 4,249,540 A | 2/1981 | Koyama et al. | |
| 4,349,034 A | 9/1982 | Ramsey, III | |
| 4,476,875 A | 10/1984 | Nilsson et al. | |
| 4,566,462 A | 1/1986 | Janssen | |
| 4,590,948 A | 5/1986 | Nilsson | |
| 4,596,254 A | 6/1986 | Adrian et al. | |
| 4,719,923 A | 1/1988 | Hartwell et al. | |
| 4,754,761 A | 7/1988 | Ramsey, III et al. | |
| 4,880,013 A | * 11/1989 | Chio | 600/485 |
| 5,030,956 A | 7/1991 | Murphy | |
| 5,072,733 A | 12/1991 | Spector et al. | |
| 5,094,244 A | 3/1992 | Callahan et al. | |
| 5,158,091 A | 10/1992 | Butterfield et al. | |
| 5,163,438 A | 11/1992 | Gordon et al. | |
| 5,238,000 A | 8/1993 | Electronics | |
| 5,273,046 A | 12/1993 | Butterfield et al. | |
| 5,368,039 A | 11/1994 | Moses | |
| 5,479,928 A | 1/1996 | Cathignol et al. | |
| 5,590,649 A | 1/1997 | Caro et al. | |
| 5,833,618 A | 11/1998 | Caro et al. | |
| 5,848,970 A | 12/1998 | Voss et al. | |
| 5,895,359 A | 4/1999 | Peel, III | |
| 5,904,654 A | * 5/1999 | Wohltmann et al. | 600/500 X |
| 5,916,180 A | 6/1999 | Cundari et al. | |
| 5,964,711 A | 10/1999 | Voss et al. | |
| 6,027,452 A | * 2/2000 | Flaherty et al. | 600/500 X |
| 6,176,831 B1 | 1/2001 | Voss et al. | |
| 6,270,461 B1 | * 8/2001 | Chio | 600/485 |

OTHER PUBLICATIONS

Carson, E. R. et al. (1983) "The Mathematical Modeling of Metabolic and Endocrine Systems: Model Formulation, Identification, and Validation", John Wiley & Sons, NY, pp. 185–189.

Anderson, E.A., et al. (1989) Flow–mediated and reflex changes in large peripheral artery tone in humans. Circulation 79:93–100.

Boashash, B., et al. (1987) An efficient real–time implementation of the Wigner–Ville distribution. IEEE Trans ASSP 35:1611–1618.

Drzewiecki, G.M., et al. (1985) Generalization of the transmural pressure–area relation for the remoral artery. $7^{th}$ Annual IEEE EMBS Conference 507,510.

Hoeks, A.P.G., et al. (1985) Transcutaneous detection of relative changes in artery diameter. Ultrasound in Med and Bio 11:51–59.

* cited by examiner

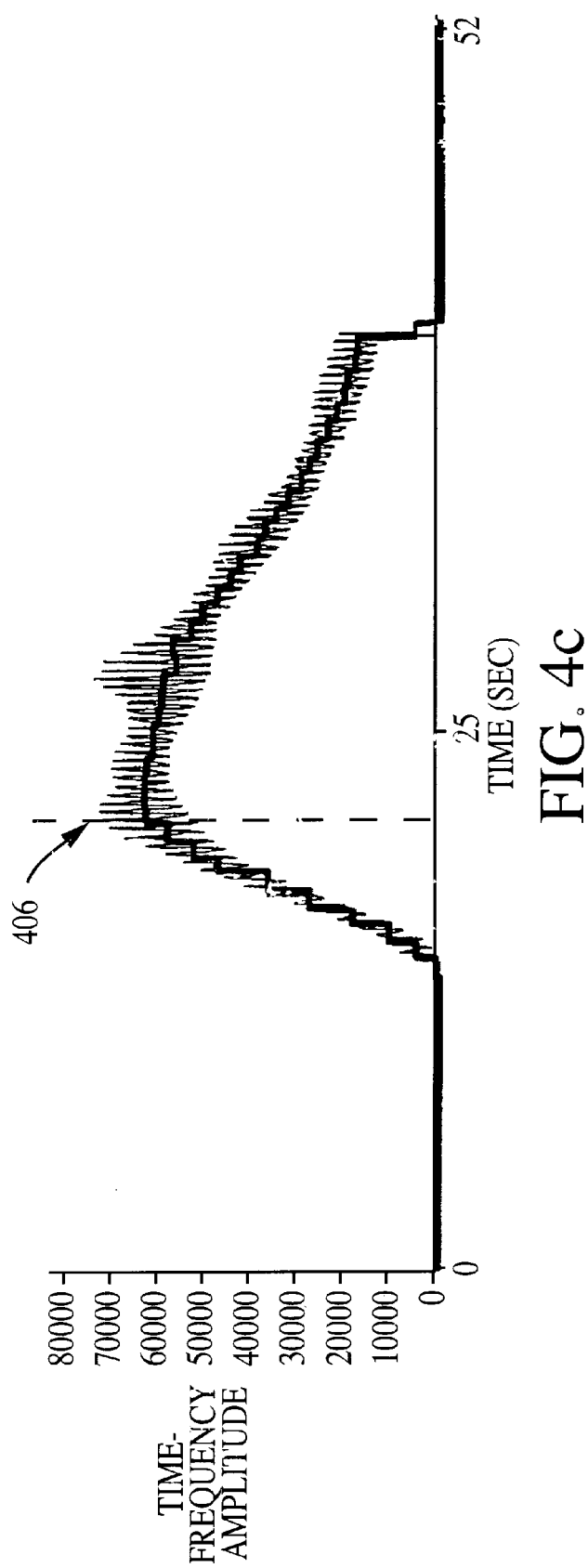

METHOD AND APPARATUS FOR THE NONINVASIVE DETERMINATION OF ARTERIAL BLOOD PRESSURE

BACKGROUND OF THE INVENTION

1. Field of the Invention

This invention relates generally to methods and apparatus for monitoring the blood pressure of a living subject, and specifically to the non-invasive monitoring of arterial blood pressure using acoustic techniques.

2. Description of the Related Art

Three well known techniques have been used to non-invasively monitor a subject's arterial blood pressure waveform, namely, auscultation, oscillometry, and tonometry. Both the auscultation and oscillometry techniques use a standard inflatable arm cuff that occludes the subject's bronchial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above generally have been effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure. This theory is illustrated graphically in FIG. 1. Note that in FIG. 1, bone or another rigid member is assumed to lie under the artery.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subjects tissue overlying the artery being sensed. This has historically led to inaccuracies in the resulting transducer signals. In addition, in some cases, this incompatibility can cause tissue injury and nerve damage and can restrict blood flow to distal tissue.

Prior art tonometry systems are also quite sensitive to the orientation of the pressure transducer on the subject being monitored. Specifically, such systems show a degradation in accuracy when the angular relationship between the transducer and the artery is varied from an "optimal" incidence angle. This is an important consideration, since no two measurements are likely to have the device placed or maintained at precisely the same angle with respect to the artery.

Perhaps the most significant drawback to arterial tonometry systems in general is their inability to continuously monitor and adjust the level of arterial wall compression to an optimum level of zero transmural pressure. Generally, optimization of arterial wall compression has been achieved only by periodic recalibration. This has required an interruption of the subject monitoring function, which sometimes can occur during critical periods. This disability severely limits acceptance of tonometers in the clinical environment.

It is also noted that the maximum pulsatile theory described above has only been demonstrated to date in excised canine arteries, and not in vivo. See, for example, Drzewiecki, G. M, et al, "Generalization of the transmural pressure-area relation for the femoral artery", $7^{th}$ *Annual IEEE EMBS Conference*, 1985, pp.507–510. Accordingly, the maximum peak-to-peak amplitude in vivo may not occur at the arterial pressure at which the transmural pressure equals zero. In fact, during anecdotal studies performed by the applicant herein using two prior art tonometry systems (with which several hundred applanation sweeps were recorded under numerous test conditions), the maximum pulsatile theory described above never yielded measured mean arterial pressure (MAP) that was consistently similar to the average of two cuff pressure measurements taken immediately before and after the sweep. These factors suggest that prior art maximum pulsatile theory devices may produce significant errors in measured MAP.

Based on the foregoing, there is a clear need for an apparatus, and related method, for non-invasively and continually monitoring a subject's arterial blood pressure, with reduced susceptibility to noise and subject movement, and relative insensitivity to placement of the apparatus on the subject. Such an improved apparatus and method would also obviate the need for frequent recalibration of the system while in use on the subject. Furthermore, it would be desirable to make certain components of the apparatus in contact with the subject disposable, thereby allowing for the cost effective replacement of these components at regular intervals.

SUMMARY OF THE INVENTION

The invention disclosed herein addresses the foregoing needs by providing an improved apparatus and method for non-invasively monitoring the arterial blood pressure of a subject.

In a first aspect of the invention, a method of measuring the blood pressure within a blood vessel of a subject is disclosed. The method generally comprises: compressing at least a portion of the blood vessel to a varying degree as a function of time; transmitting an acoustic wave into the blood vessel during compressing; receiving an echo of the acoustic wave from the blood vessel during compressing; estimating at least one parameter based on the echo by forming a time-frequency distribution of the echo; and determining the pressure within the blood vessel when the parameter is estimated to satisfy a predetermined condition. In one exemplary embodiment, both pressure and ultrasonic transducers are placed over the blood vessel. Blood velocity and time-frequency distribution are determined as a function of time and the peak time-frequency distribution is correlated to the mean arterial pressure (MAP).

In a second aspect of the invention, the foregoing acoustic pulses are used to assist in placement of the transducers on the subject's wrist so as to maximize the signal-to-noise ratio associated with the blood pressure measurement. In one embodiment, the amplitude of echoes received by the ultrasonic transducer is measured by an ultrasound receiver circuit as the transducer is moved transversely across the artery of interest; the transducer is positioned using a fuzzy logic control circuit such that the amplitude of the echoes is minimized.

In a third aspect of the invention, an improved blood pressure monitoring device is disclosed. The device generally comprises: first apparatus adapted to compress a blood vessel of subject and measure the pressure applied thereto; second apparatus adapted to transmit acoustic energy into the blood vessel and receive at least one echo resulting therefrom; and a processor operatively coupled to the first and second apparatus and configured to process the measured pressure and the at the compression of at least a portion of the blood vessel; (ii) transmit the acoustic energy into the blood vessel and receive the at least one echo therefrom during at least a portion of the act of varying the compression; (iii) form a time-frequency representation of the at least one echo using at least the processor; and (iv) determine the pressure within the blood vessel when the representation satisfies a given condition. In one exemplary embodiment, a pressure transducer and an ultrasonic transducer are contained within a common unit worn on the subject's wrist, and measure both the arterial applanation and arterial blood velocity. The time-frequency distribution is determined from the velocity data, as calculated by an algorithm running on a digital signal processor (DSP). The time at which the time-frequency distribution is maximized corresponds to the time at which the transmural pressure equals zero, and the mean pressure read by the pressure transducer equals the MAP.

In a fourth aspect of the invention, an improved applanation and transverse positioning motor assembly is disclosed for use with the above described tonometric apparatus. In one embodiment, the assembly includes a first motor for applanation (compression) of the artery in response to fuzzy logic signals from a control circuit, as well as a second motor operatively connected to an ultrasonic receiver (and associated fuzzy logic control circuit) for transverse positioning of the transducer(s) over the artery. The motor assembly is coupled to the transducers and rigidly received within a wrist brace described below such that the applanation motor exerts compressive force against the subject's artery via reaction force against the wrist brace.

These and other features of the invention will become apparent from the following description of the invention, taken in conjunction with the accompanying drawings.

BRIEF DESCRIPTION OF THE DRAWINGS

FIG. 3b is a block diagram illustrating a first embodiment of the method of estimating the time-frequency distribution used in conjunction with the method of FIG. 3a.

FIGS. 4a–4c are exemplary plots illustrating the relationship between pressure and time, blood velocity and time, and time-frequency distribution and time, respectively, based on typical data obtained using the method of FIGS. 3a–3b.

DETAILED DESCRIPTION OF THE INVENTION

Reference is now made to the drawings wherein like numerals refer to like parts throughout.

It is noted that while the invention is described herein in terms of a method and apparatus for monitoring arterial blood pressure suitable for use on the radial artery (i.e., wrist) of a human subject, the invention may also conceivably be embodied or adapted to monitor arterial blood pressure at other locations on the human body, as well as monitoring blood pressure on other warm-blooded species. All such adaptations and alternate embodiments are considered to fall within the scope of the claims appended hereto.

Figure 1:
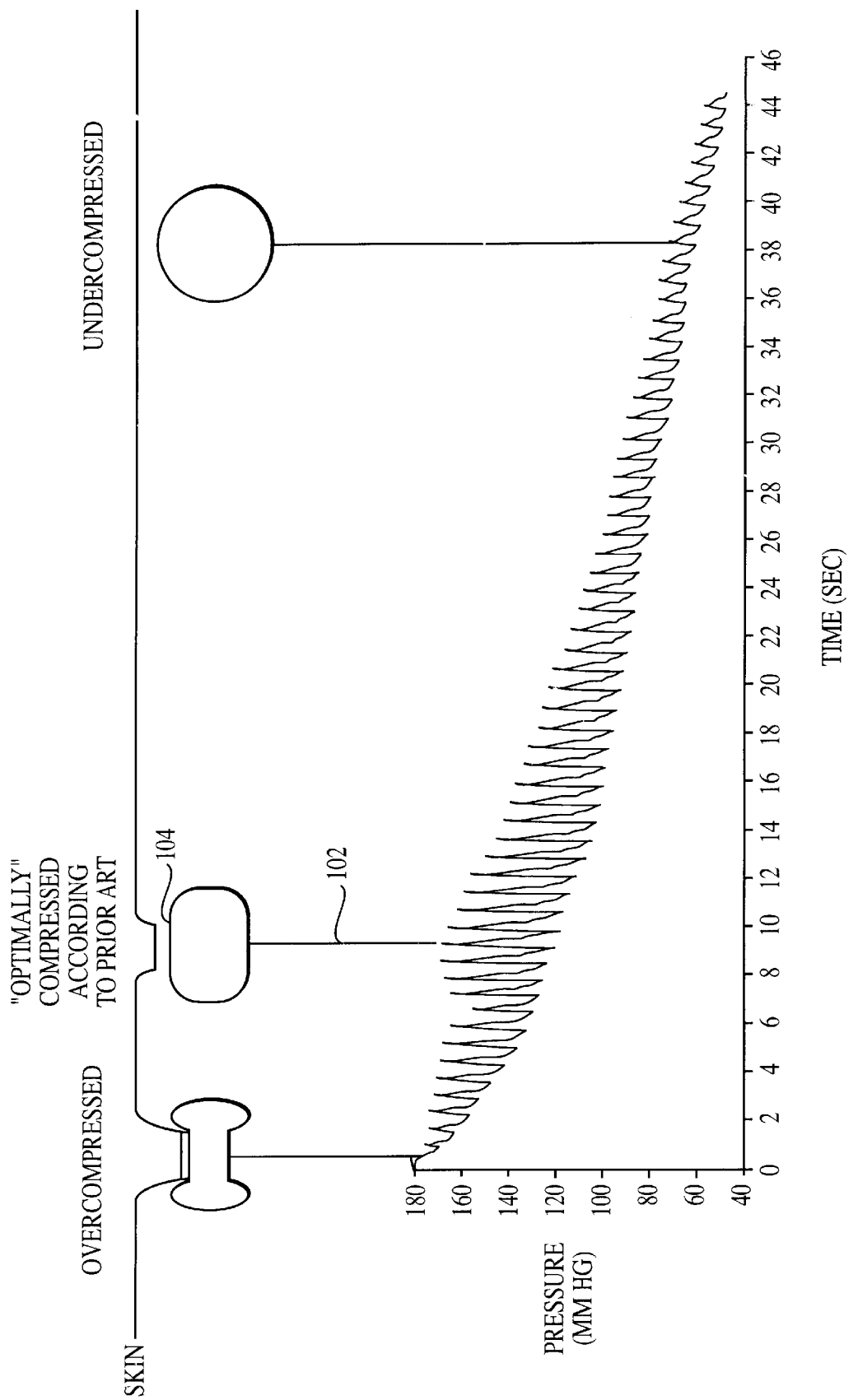
FIG. 1 is a composite graph illustrating the cross-sectional shape of an artery as a function of applied pressure and time, as correlated to blood pressure waveforms, according to prior art arterial tonometry theory.
Figure 2:
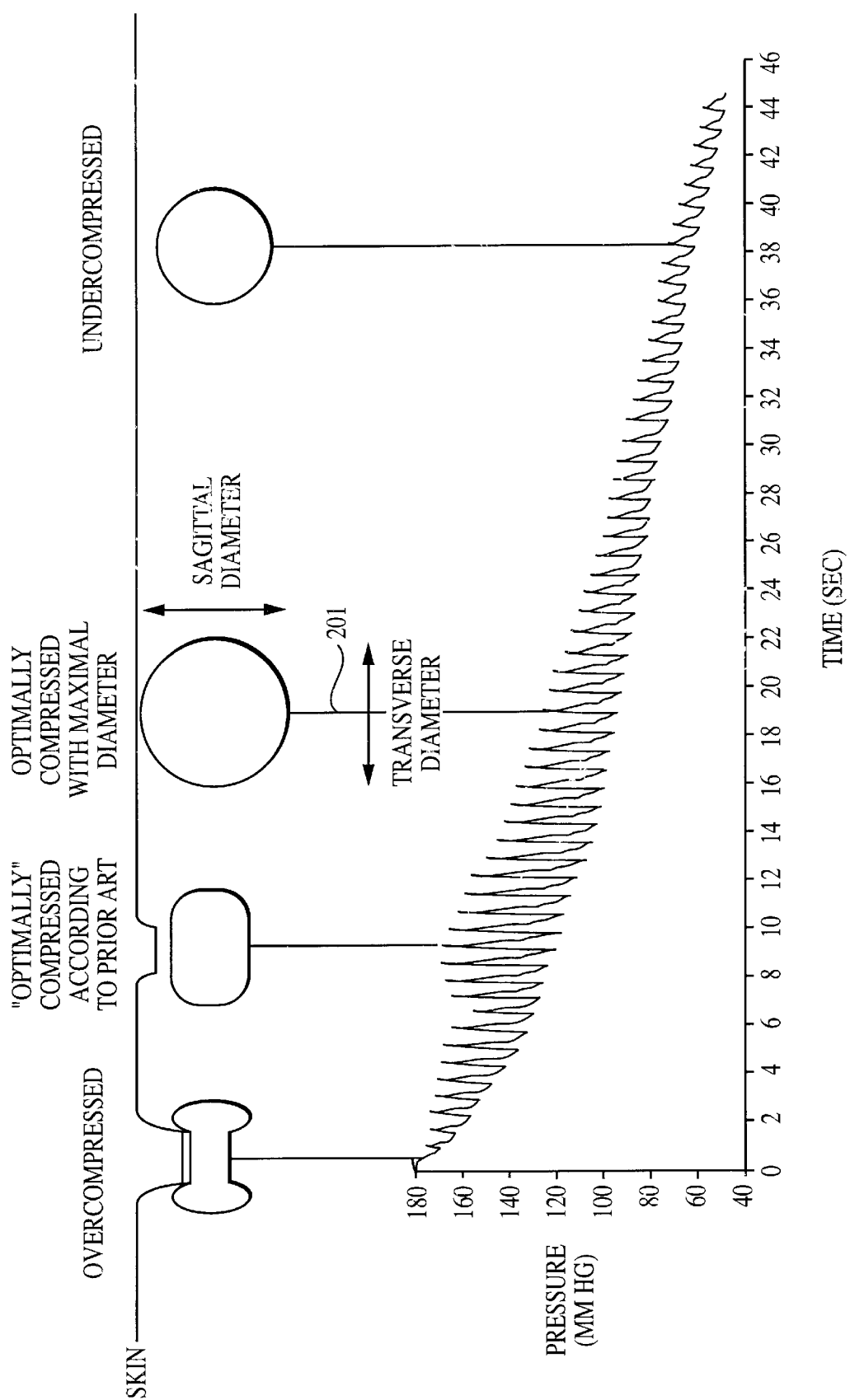
FIG. 2 is a composite graph illustrating the cross-sectional shape of an artery as a function of applied pressure and time, illustrating the hypothesized mechanism behind the maximum time-frequency distribution applanation concept of the present invention.

Referring now to FIGS. 1 and 2, the hypothesized maximum arterial diameter applanation concept of the present invention is described. Under the prior art tonometry theory previously described with respect to FIG. 1, the maximum pulsatile pressure is assumed to correspond to the state of zero transmural pressure; i.e., the point in time 102 when the arterial pressure is perpendicular to the arterial wall surface 104 and is the only pressure detected by the tonometer pressure transducer (not shown). Hence, prior art tonometry systems utilizing this theory measure the maximum peak-to-peak blood pressure within the artery, and correlate this pressure to a state of zero transmural pressure.

In the invention disclosed herein, however, the optimum applanation is found by evaluating one or more other parameters rather than detecting the maximum pulsatile pressure as in the prior art; i.e., in one embodiment, the invention estimates the maximum time-frequency distribution during an applanation sweep. The maximum time-frequency distribution may be indicative of, inter alia, the maximum arterial diameter. As used herein, the term "diameter" includes the actual diameter of a blood vessel measured in a particular dimension or direction and at a particular point in time, as well as any related parameters calculated based on the actual diameter to include, without limitation, mean diameter calculated over a particular time interval, mean diameter as a function of position on the blood vessel, and maximum diastolic diameter (Appendix A). In the maximum time-frequency method of the present invention, it is hypothesized that the optimum applanation occurs at that point in time 201 during the applanation sweep when the external applied pressure has decreased sufficiently so that internal pressure may oppose it, allowing the sagittal arterial diameter to transiently increase to its maximum as a consequence of reactive hyperemia. This phenomenon may occur at the true mean arterial pressure, during which the transmural pressure equals zero, as shown in FIG. 2.

Method of measuring Mean Arterial Pressure (MAP)

Figure 3A:
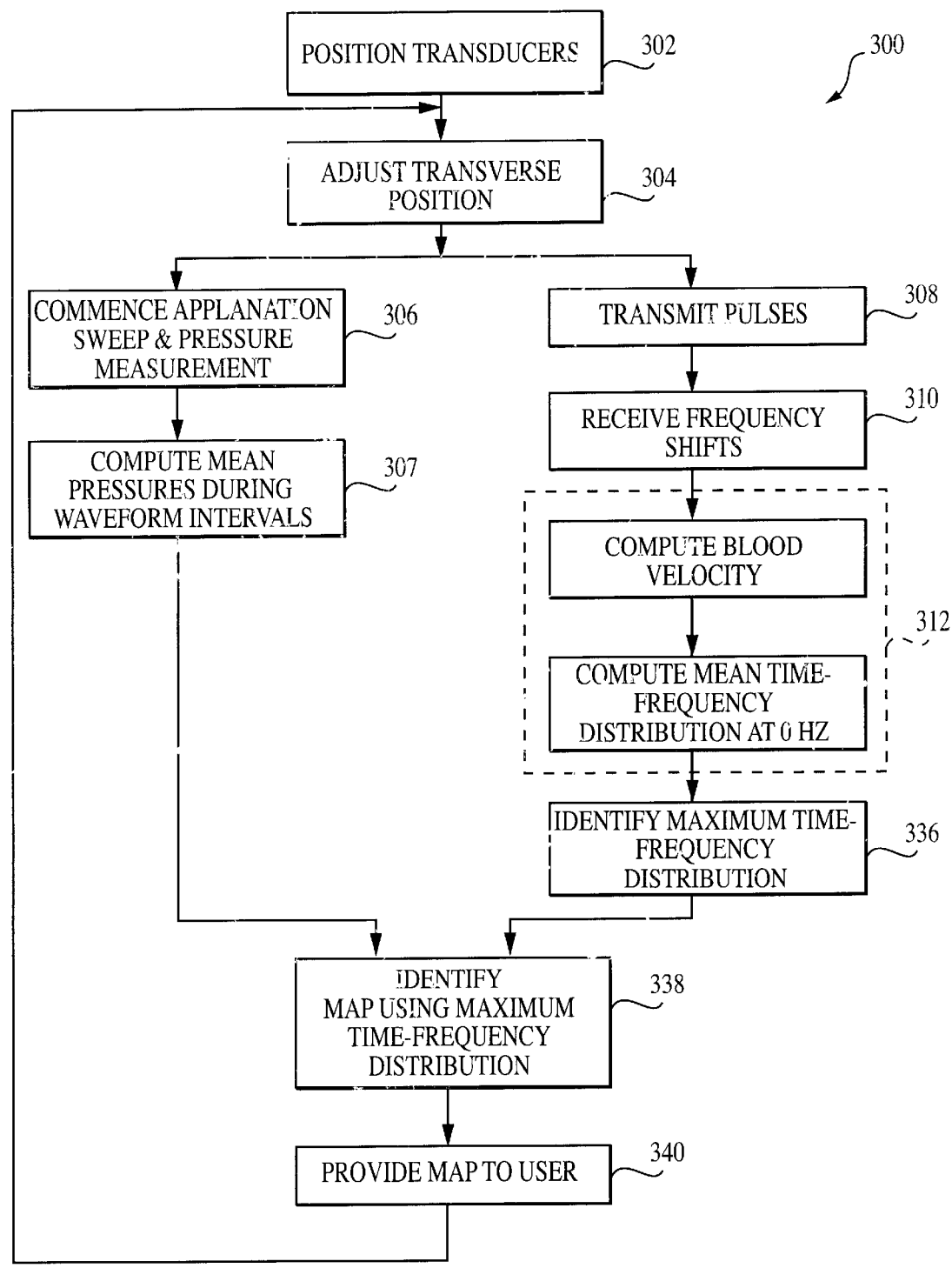
FIG. 3a is a block diagram illustrating one embodiment of the method of measuring arterial blood pressure according to the present invention.

Referring now to FIG. 3*a*, one embodiment of the maximum time-frequency method of measuring mean arterial pressure according to the present invention is described. In the method 300 of FIG. 3*a*, pressure and ultrasonic transducers (described in greater detail below with reference to FIGS. 5, 6, and 7) are first positioned generally atop the radial artery of the subject in step 302. As is well known in the medical sciences, the radial artery in the human being runs longitudinally along the inner surface of the wrist and forearm below the surface tissue. Very precise transverse positioning of the ultrasonic and pressure transducers is accomplished in step 304 by generating a series of acoustic pulses, which produce echoes via interaction with tissue and/or red blood cells present in the artery. The amplitude of these echoes is measured as a function of position, and the transverse position of the transducer element is adjusted so that the amplitude is minimized. At the position overlying the center of the artery, the echoes are mostly absorbed by the blood, as compared to absorption by tissue. Exact positioning over the artery increases the signal-to-noise ratio (SNR) and therefore accuracy of the blood pressure measurement.

Next, in step 306, a decreasing applanation sweep of the selected artery is commenced. The applanation sweep begins by overcompressing the artery against the underlying bone (or other rigid member) using the aforementioned pressure transducer such that a cross section similar to that shown in FIG. 2 is obtained. As the sweep progresses, the compression of the artery is gradually reduced until the artery is ultimately not compressed at all. During the progression of the applanation sweep, the pressure within the artery during each heartbeat is measured using the pressure transducer, and the mean value of each pressure waveform computed in step 307. Concurrently with the applanation sweep of step 306, acoustic pulses are generated and transmitted into the artery using the ultrasonic transducer in step 308. These pulses are reflected by various structures or entities within the artery (such as the artery walls, and the red blood cells within the subject's blood), and subsequently received as frequency shifts by the ultrasonic transducer in step 310. Next, in step 312, the blood velocity and time-frequency distribution are calculated using the received frequency shifts. Specifically, the frequencies of those echoes reflected by blood cells within the blood flowing in the artery will differ from that of the transmitted acoustic pulses due to the motion of the blood cells. This well known "Doppler shift" in frequency is used to calculate the blood velocity. Other components of the transmitted pulse are reflected by effectively stationary objects (such as the arterial walls 104); the phase of these echoes is used to calculate the time-frequency distribution. The calculation of the blood velocity and time-frequency distribution are described in greater detail below with respect to FIGS. 3*b* and 3*c*. The mean time-frequency distribution at 0 Hz is computed during each heartbeat in step 312. In step 336, the mean time-frequency distribution measurements obtained in step 312 are analyzed to locate the maximum mean time-frequency value occurring during the applanation sweep; the mean arterial pressure corresponding to the maximum time-frequency distribution is then identified in step 338. This mean arterial pressure value is then provided to the user as the MAP in step 340.

Figure 3B:
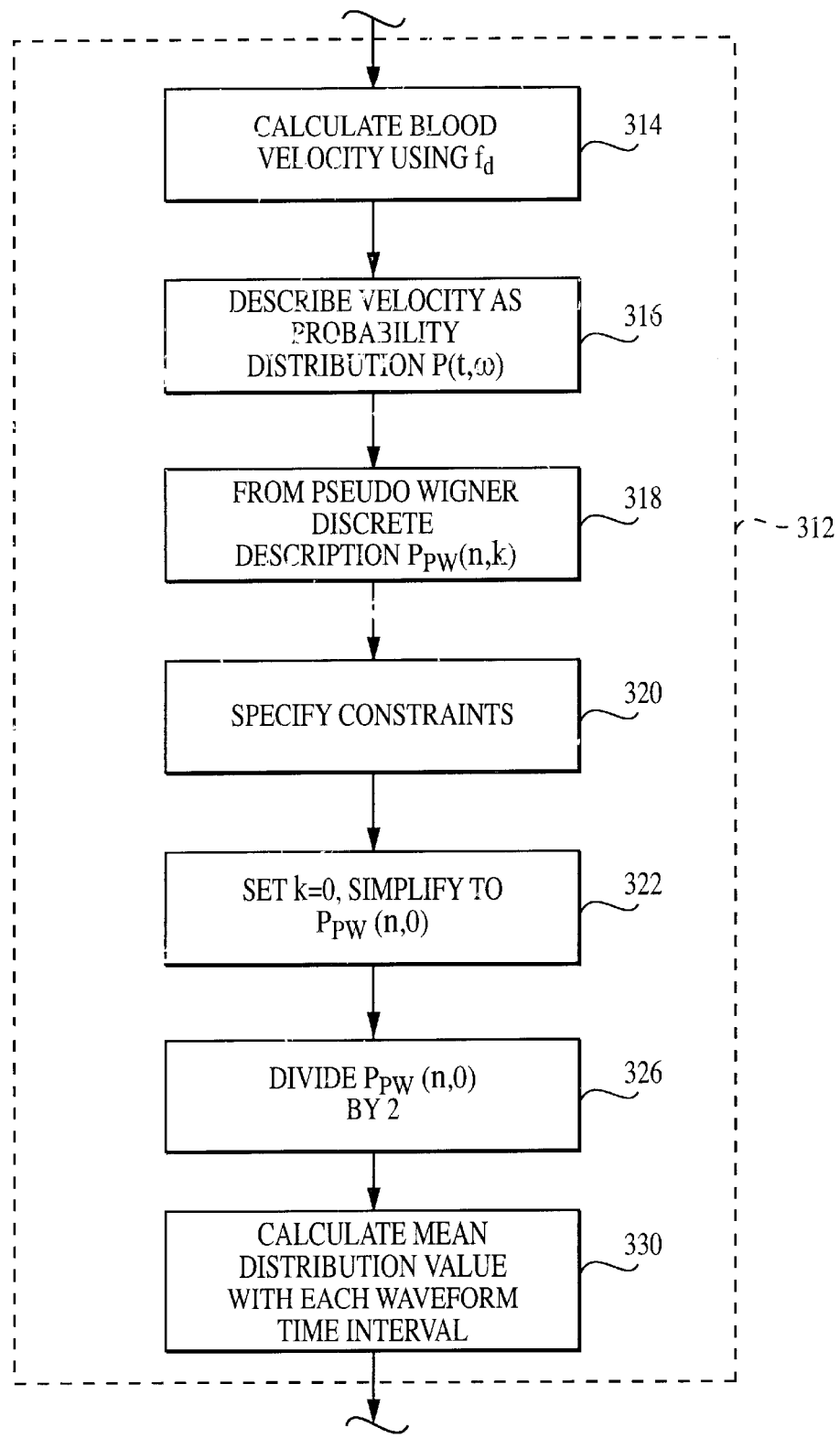

Referring now to FIG. 3*b*, a first embodiment of the method of determining blood velocity and time-frequency distribution according to the invention is described. As shown in FIG. 3*b*, the first sub-step 314 of step 312 comprises using the Doppler frequency, fd, and Eqn. 1 to obtain the mean blood velocity, $|\overline{V}|$:

$$|\overline{v}| = \frac{f_d c}{2 f_o \cos\theta}, \quad \text{(Eqn. 1)}$$

where $f_o$ is the transmitted signal frequency, $\theta$ is the transmission angle of the acoustic energy referenced to a vector normal to the longitudinal axis of the artery, and c is the speed of sound in soft tissue.

In the embodiment of FIG. 3*b*, a time-frequency representation of the type well known in the mathematical arts is calculated for the blood velocity. A time-frequency representation is a two-dimensional mapping of the fraction of the energy of a one-dimensional signal at time, t, and angular frequency, $\omega$. This joint energy density, $P(t,\omega)$, is commonly referred to as a "probability distribution" or "distribution", referring to its historical utility in quantum mechanics. This distribution is described in sub-step 316 of FIG. 3 using the form shown in Eqn. 2:

$$P(t, \omega) = \frac{1}{4\pi^2} \int \int \lambda(\theta, \tau) u^*(\theta - 0.5\tau) u(\theta + 0.5\tau) e^{-j\theta t - j\tau\omega} d\theta d\tau, \quad \text{(Eqn. 2)}$$

where $d\theta$ and $d\tau$ are dummy integration variables, $\lambda(\theta,\tau)$ is a two-dimensional function known as a "kernel", and u(t) is the input signal. The simplest distribution is the Wigner or Wigner-Ville distribution, which uses a kernel of $\lambda(\theta,\tau)=1$. Note that Eqn. 2 uses continuous time, t, while an actual implementation of the distribution requires discrete time, n. Next, using discrete frequency, k, the discrete time description of the Wigner distribution (also known as a Pseudo Wigner distribution) is formed per sub-step 318 of FIG. 3*b*, as shown in Eqn. 3.

$$P_{PW}(n,k) = 2\sum_{\tau=-L}^{+L} e^{-j4\pi k\tau/N} u^*(n-\tau)u(n+\tau),\qquad \text{(Eqn. 3)}$$

where $$k = \frac{\omega}{2\pi},$$

u(t) and its complex conjugate are sample-limited to {−K/2,+K/2}, K is even, and N=K+1. Next, in sub-step 320, a rectangular window is specified, so that L =K/2−|n|. See, e.g., Boashash, B., et al, "An efficient real-time implementation of the Wigner-Ville distribution", *IEEE Trans ASSP*, 35:1611–1618, 1987, which is incorporated herein by reference in its entirety.

In sub-step 322, a frequency of k=0 Hz is selected, and the Pseudo Wigner calculation simplified to the form of Eqn. 4:

$$P_{PW}(n,0) = 2\sum_{\tau=-L}^{+L} u^*(n-\tau)u(n+\tau).\qquad \text{(Eqn. 4)}$$

Eqn. 4 is equivalent to direct integration of the autocorrelation of a signal, scaled by a factor of 2. Autocorrelation is well known in the signal processing arts. In sub-step 326, Eqn. 4 is divided by a factor of 2. Lastly, in sub-step 330, the mean distribution value is calculated for each heartbeat or pressure waveform time interval.

It is noted that various features in the time-frequency distribution calculated using the method 300 of FIG. 3a can be emphasized by specifying a different kernel. For example, using the kernel $\lambda(\theta,\tau)=e^{-\theta^2\tau^2/\sigma}$, where $\sigma$ is a parameter, to calculate the Choi-Williams distribution, the time-frequency fluctuations within each heartbeat would be reduced. Feature analysis at other frequencies is also possible since similar mean distributions are calculated, but at the expense of more complicated computations. This flexibility in feature selection further enhances the utility of the time-frequency distribution in the present embodiment.

Figure 4A:
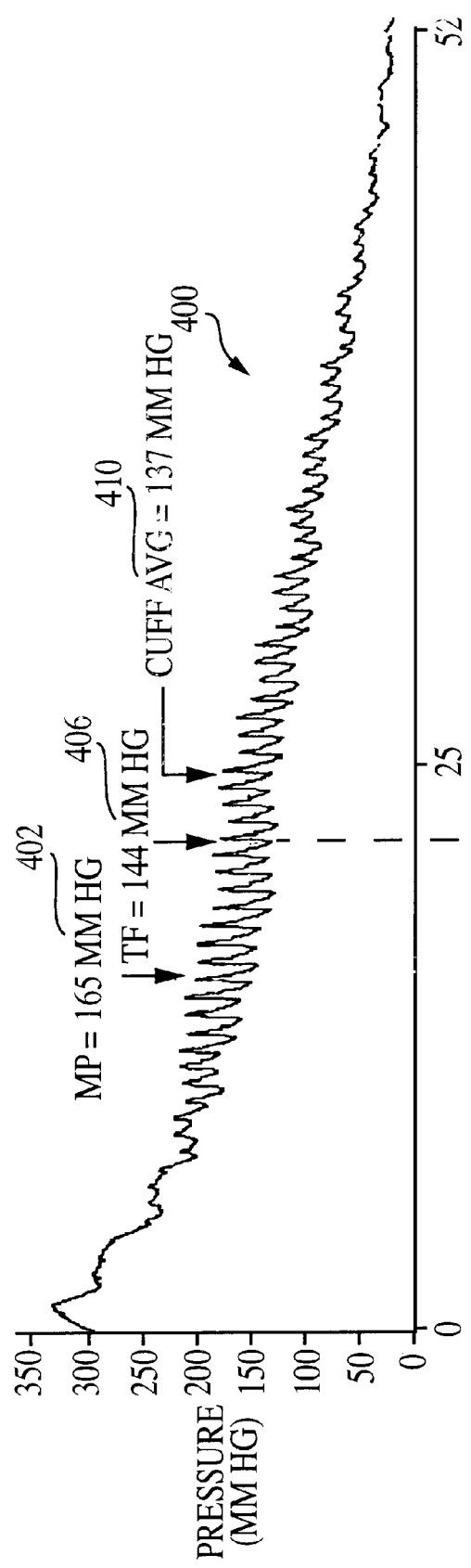
Figure 4B:
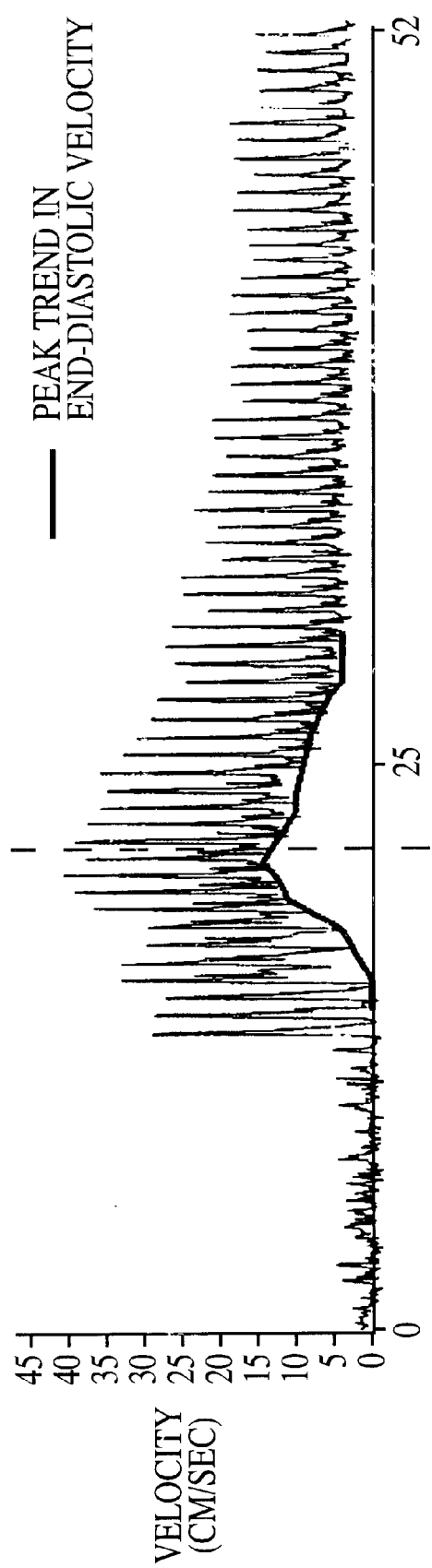

FIGS. 4a–4c are exemplary plots illustrating the relationship between measured radial arterial blood pressure and time (FIG. 4a), radial blood velocity and time (FIG. 4b), and the Pseudo Wigner distribution and time (FIG. 4c), based on typical data obtained using the method of FIG. 3a. The characteristic peak in the Pseudo Wigner distribution results from a large peak trend in the baseline of the blood velocity signal, also known as the end-diastolic velocity (FIG. 4b). In other arteries such as the bronchial and femoral arteries, it is known that a similar peak trend in the end-diastolic velocity can be induced after complete arterial occlusion with a cuff for several minutes, followed by complete cuff release. The transient increase in blood flow that follows a brief arterial occlusion is called reactive hyperemia. This transient increase in blood flow and end-diastolic velocity is known to induce a transient increase of 19% in bronchial arterial diameter. See, e.g., Anderson, E., et al, "Flow-mediated and reflex changes in large peripheral artery tone in humans", *Circulation*, 79:93–100, 1989, which is incorporated herein by reference in its entirety.

While the radial artery is not compressed by a cuff at the beginning of a decreasing applanation sweep, its flow is completely occluded by the pressure/ultrasound sensor. As the compression decreases during the course of a sweep, reactive hyperemia and its signature peak trend in end-diastolic velocity are induced. The accompanying transient increase in arterial diameter occurs transversely across the artery, but is probably initially prevented sagitally (top to bottom) by the external pressure exerted by the sensor. However, as this external pressure decreases during the sweep to the true mean arterial pressure, the opposing pressure within the artery becomes sufficient that the sagittal arterial diameter may also now increase. The increase in sagital arterial diameter would occur when the transmural pressure equals zero.

The peak in the Pseudo Wigner distribution at a frequency of 0 Hz may indicate when this sudden arterial diameter increase occurs. From Eqn. 1, it is known that the mean blood velocity is proportional to the Doppler shift frequency. The angular frequency of the received wave, $\omega_d$, is found using Eqn. 5:

$$\omega_d = 2\pi f_d.\qquad \text{(Eqn.5)}$$

The angular frequency $\omega_d$ is integrated; this integration results in the phase of the detected signal echo, $\phi$, as illustrated in Eqn. 6:

$$\phi = \int \omega_d dt.\qquad \text{(Eqn.6)}$$

As is well known in the art, the low frequencies in the phase echo are proportional to the relative arterial diameter of the artery, d. See, e.g., Hoeks, A. P. G., et al, "Transcutaneous detection of relative changes in artery diameter" *Ultrasound Med & Biol*, 11:51–59, 1985. The phase $\phi$ of the detected echo is a function of the time delay between reflection from the near and far arterial walls. Because the time delay depends only on the time difference between reflections from the two arterial walls, the measurement is insensitive to transmission angle. Note that only the relative arterial diameter changes from an initial diameter value during overcompression can be estimated. The relative arterial diameter d is therefore related to the phase using Eqn. 7:

$$d = \frac{\phi c}{4\pi f_o} = \frac{c}{f_o}\int f_d dt = \cos\theta \int |\overline{v}|dt.\qquad \text{(Eqn. 7)}$$

Referring back to the Pseudo Wigner distribution calculation at 0 Hz in Eqn. 4, this discrete summation is equivalent to the continuous integral in Eqn 7. As the constant 2 in Eqn. 4 and cos θ in Eqn. 7 are only scale factors and u(n)=|$\overline{v}$(n)|, the Pseudo Wigner distribution at 0 Hz is equivalent to the proportional squared relative arterial diameter. Therefore, the peak distribution may occur at the sudden change in sagittal arterial diameter when MAP is reached (FIG. 2). The distribution is smooth, rather than discontinuous at the peak, because the time-frequency distribution acts as a smoothing filter.

Figure 3C:
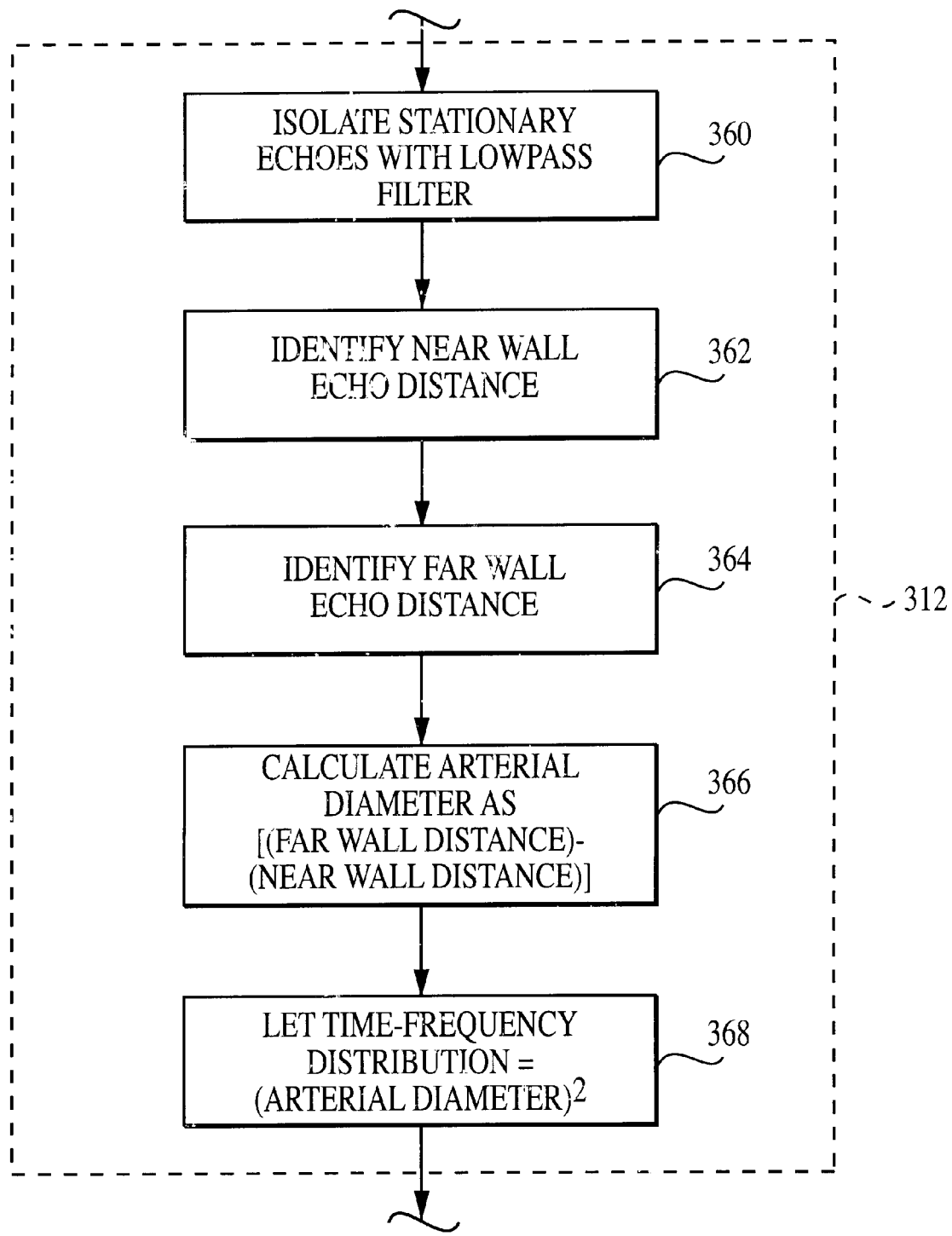
FIG. 3c is a block diagram illustrating a second embodiment of the method of estimating the time-frequency distribution.

Based on this maximum arterial diameter hypothesis, a second embodiment of the method of calculating blood velocity and arterial diameter in conjunction with step 312 of FIG. 3a is now described with respect to FIG. 3c. Rather than calculate the maximum mean time-frequency distribution, diameter changes can be calculated by monitoring the sagittal near and far walls directly. First, stationary echoes are obtained in step 360 using a lowpass filter. The sagittal near and far wall echoes are identified in steps 362 and 364, respectively, and the distance between them is used to calculate the arterial diameter over time in step 366. Finally, in step 368, the time-frequency distribution is equated to the square of the arterial diameter. Note that while this method of calculating the arterial diameter may detect a sudden diametric change more quickly than the time-frequency based method illustrated in FIG. 3b, it is also more complicated because the near and far walls must be continuously detected. See also the discussion of FIGS. 5a and 5b below, which illustrate two exemplary ultrasound filter circuits useful in performing the analysis of FIG. 3c.

It is noted that many variations of the methods described above with reference to FIGS. 3a–3c may be utilized consistent with the invention. Specifically, certain steps are optional and may be performed or deleted as desired. For example, a discrete frequency other than k=0 may be used in step 322. Similarly, other steps (such as additional data sampling or mathematical analysis for example) may be added to the foregoing embodiments. Additionally, the order of performance of certain steps may be permuted, or performed in parallel (or series) if desired. The foregoing methods of FIGS. 3a–3c are therefore merely illustrative of the broader methods of the invention disclosed herein.

The application of the method of FIGS. 3a–3b to typical data is set forth in Appendix A hereto, and illustrated in the exemplary plots of FIGS. 4a–4c. As shown in FIG. 4a, the measured arterial blood pressure 400 generally declines with time, due to reduced applanation of the artery. Note that at some time after beginning the applanation sweep, in this example after approximately 15 seconds, the maximum pulsatile pressure (i.e., the largest peak-to-peak pressure difference) is experienced. At this point, the mean arterial blood pressure (MAP) 402 is approximately 165 mm Hg. At some further time, in this example after approximately 21 seconds, the mean time-frequency distribution (FIG. 4c) is maximized, and the MAP 406 (FIG. 4a) is approximately 144 mm Hg. At a third time, in this example after approximately 24 seconds, the MAP measured during tonometric applanation 410 is closest to the average MAP measured using a prior art oscillometry device, at 137 mm Hg. Hence, based on the data presented in FIG. 4a, prior art maximum pulsatile techniques are substantially less accurate than the "maximum time-frequency" method of the present invention. More significantly, the maximum time-frequency method disclosed herein provides an excellent approximation of the actual mean arterial pressure (as measured by an oscillometry device). Note that noninvasive oscillometry measurement itself possesses an error when compared to the invasive gold standard measurement that utilizes an intra-arterial pressure catheter.

It should also be noted that the "maximum mean time-frequency" method disclosed herein is substantially insensitive to the orientation of the ultrasonic transducer with respect to the artery. As further detailed in Appendix A, numerous anecdotal measurements obtained by the applicant herein showed little variation under a broad range of angular pitch (i.e., rotation around an axis transverse to the longitudinal axis of the artery being measured) and roll (i.e., rotation around the longitudinal axis of the artery) values. It will be readily appreciated that such insensitivity affords great advantages to the user, since consistent results may be obtained with essentially no consideration to the angular position of the tonometric sensor(s).

Figure 5A:
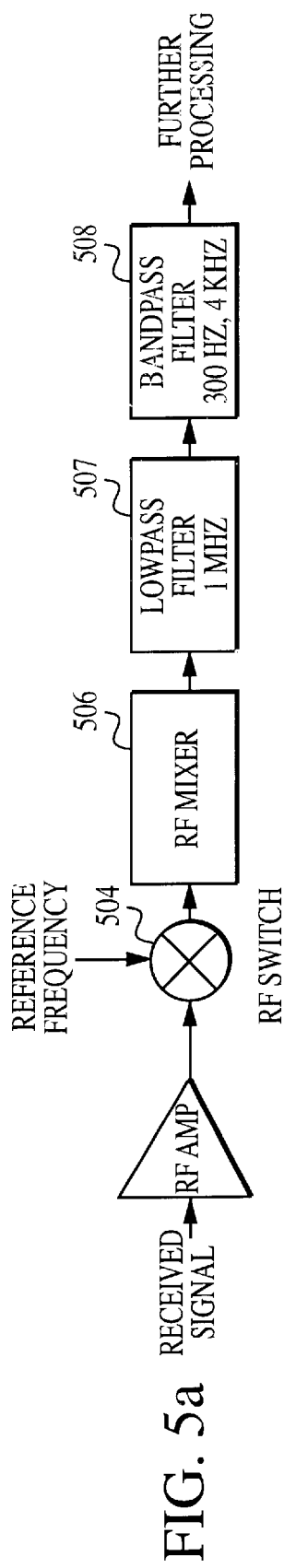
FIGS. 5a–5b are functional block diagrams of two embodiments of ultrasound filter circuits useful for measurement of Doppler shift frequencies and stationary echoes.
Figure 5B:
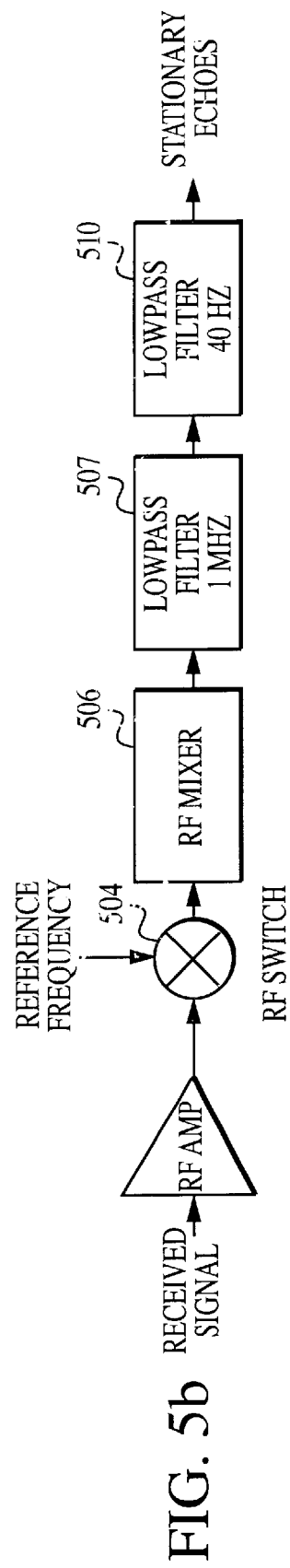

Referring now to FIGS. 5a–5b, two exemplary embodiments of the Doppler ultrasound filtering circuit used in conjunction with the method of FIG. 3c are described. In the embodiment 500 of FIG. 5a, the received signal is amplified, and supplied to a radio frequency (RF) switch 504. The switch gates the signal to the RF mixer 506, which mixes the gated bursts with the original transmission frequency. Through this demodulation scheme, the Doppler shift frequencies are isolated. A lowpass filter of 1 MHz 507 is applied to remove the signal sideband frequencies and noise, although it will be appreciated that other filter frequencies may be used. A bandpass filter 508 with a cutoff frequencies of 300 Hz and 4 kHz is then applied to remove unwanted echoes from stationary tissue such as arterial walls. The output of the bandpass filter is further processed to obtain the mean Doppler shift frequencies.

In the embodiment of FIG. 5b, for direct calculation of arterial diameter, this bandpass filter can be replaced by a lowpass filter 510 with a cutoff of 40 Hz that isolates stationary echoes. The near and far walls would be identified from the stationary echoes and used to calculate changes in arterial diameter.

Arterial Blood Pressure Measuring Apparatus

Figure 6:
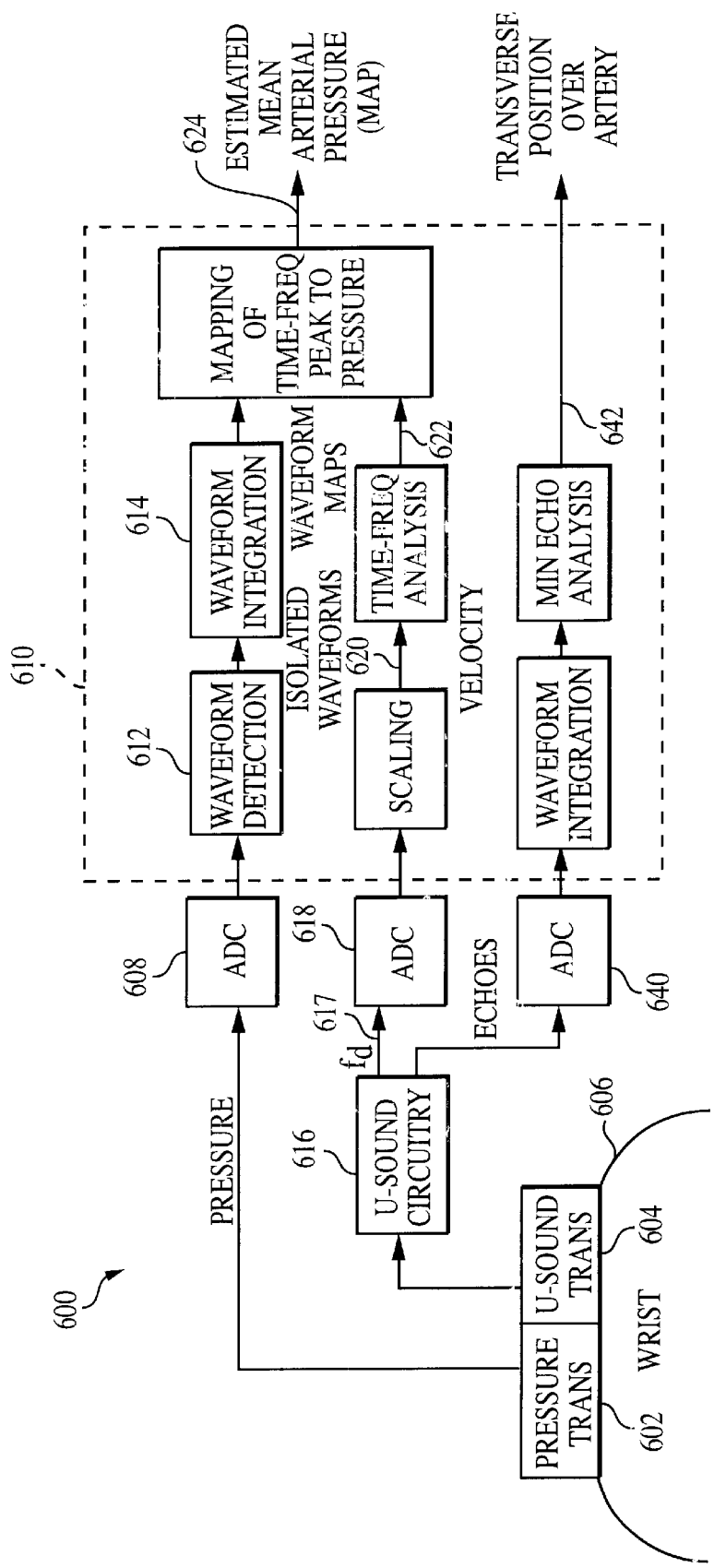
FIG. 6 is a functional block diagram of one embodiment of the arterial blood pressure monitoring device of the present invention.

Referring now to FIG. 6, one embodiment of the blood pressure measuring system according to the invention is described. As shown in FIG. 6, the system 600 comprises pressure and ultrasonic transducers 602, 604 which are placed in contact with the skin of the subject 606 during use. The pressure transducer 602 of the present embodiment is a silicon transducer of the type well known in the electrical arts, although other may be used. It will be recognized that the term "transducer" as used herein is meant to include any type of sensor capable of sensing or receiving one parameter and generating or transmitting a signal based thereon, or alternatively capable of receiving a signal and generating some physical response thereto.

Pressure applied to the face of the transducer is converted to an electrical signal bearing a known relationship thereto. The pressure transducer 602 is connected to a first analog-to-digital converter (ADC) 608, which converts the analog signal generated by the pressure transducer 602 to a digital representation. In the present embodiment, a 12-bit ADC is used, although it will be appreciated that other types may be substituted. The digitized pressure signal is then supplied to a digital signal processor (DSP) 610. Within the processor, each pressure waveform is detected using wavelet transforms 612. Wavelet transforms are known to those skilled in the art to easily detect edges, or in this case the onset of new waveforms, while noise is present. Each isolated waveform is then integrated to determine its mean arterial pressure value 614.

The ultrasonic transducer 604 generates and transmits an acoustic wave based on a first electrical signal applied thereto, and subsequently generates a second electrical signal upon receiving pressure waves in the form of echoes resulting from the transmitted acoustic waves. The first electrical signal is generated via an ultrasonic driving and receiving circuit 616, which is described in greater detail with reference to FIG. 7. The driving and receiving circuit 616 generates electrical pulses which, when applied to the transducer 604, produce acoustic energy having a frequency on the order of 8 MHz, a pulse width or duration of approximately 8 microseconds, and a pulse repetition interval (PRI) of approximately 16 us, although other values of frequency, pulse width, and PRI may be used. Hence, the transducer 604 of the present embodiment emits an 8 microsecond pulse, which is followed by an 8 microsecond "listen" period, every 16 microseconds. The echoes from these pulses are received by the ultrasonic transducer 604 during the listen period. The ultrasonic transducer 604 of the present embodiment is a ceramic piezoelectric device of the type well known in the art, although other types may be substituted. The transducer 604 converts the received acoustic signal to an electrical signal, which is then supplied to the receiving section of the ultrasonic driver and receiver circuit 616, which contains two receiver circuits. The output of the first receiver circuit is an analog signal representative of the Doppler frequency $f_d$ of the echo received by the transducer

604. The analog output 617 is then converted to a digital representation by a second ADC 618, and supplied to the DSP 610. Within the DSP, the digitized Doppler frequency is scaled to compute the blood velocity 620 within the artery $|\overline{v}|$ based on the Doppler frequency $f_d$, as described above. The time-frequency distribution of the blood velocity 622 is then computed. Finally, the DSP maps in time the peak of the time-frequency distribution to the corresponding pressure waveform to produce the estimated MAP 624, based on the method of FIG. 3a described above.

The output of the ultrasonic receiver circuit 616 is an analog echo signal proportional to absorption of the transmitted frequencies by blood or tissue. This analog signal is converted to a digital representation by a third ADC 640 and supplied to the DSP 610. Within the DSP, each group of echoes, generated for a different transversal position, is integrated to determine a mean value 642. The mean echo values are compared to determine the minimum value, which is caused by direct positioning over the artery.

The use of such algorithms running on digital signal processing devices (such as the DSP 610) to perform mathematical calculations is well known in the signal processing arts, and accordingly will not be described further herein. The DSP's output signal is then converted to a form useful to the user such as a digital or analog display, computer data file, or audible indicator.

Figure 7:
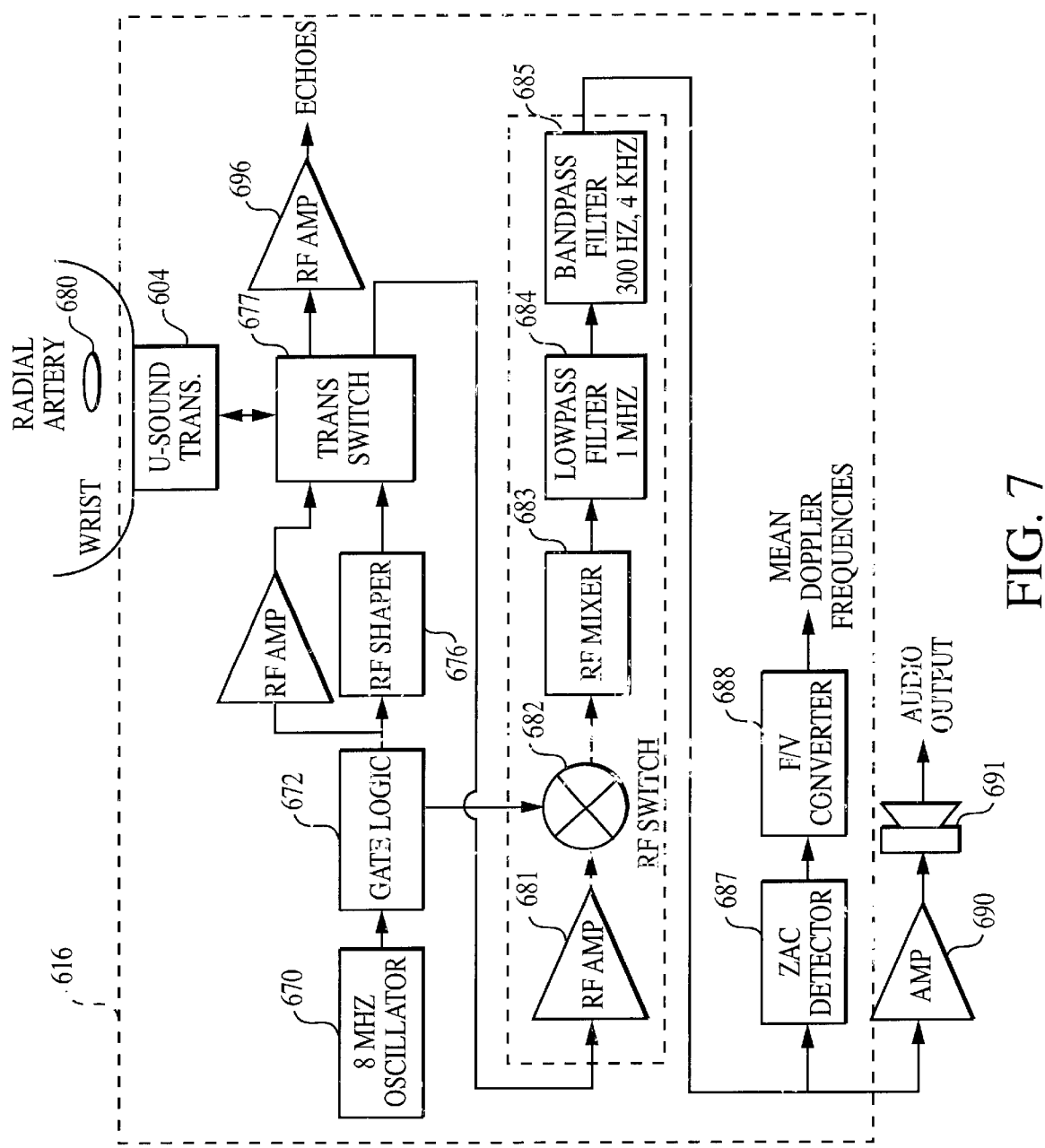
FIG. 7 is a block diagram of one embodiment of the ultrasound receiver circuit used in conjunction with the blood pressure monitoring device of FIG. 6.

Referring now to FIG. 7, which incorporates the ultrasonic filtering circuit of FIG. 5a, one embodiment of the ultrasonic driver and receiver circuit 616 is now described. As shown in FIG. 7, an oscillator 620 generates a continuous square wave signal, having a fixed frequency of 8 MHz, for coupling to a gate logic circuit 672 and to an RF mixer 674. The gate logic circuit transmits 8 us bursts of the 8 MHz signal, interrupted by 8 microsecond dead times. An RF shaper circuit 676 converts the resulting series of square wave bursts from the gate logic circuit 672 into corresponding sine wave bursts, for application through a transducer switch 677, to the ultrasonic transducer 604. The transducer switch 677 routes ultrasonic signals for both applanation and transverse positioning. The ultrasonic transducer 604 is thereby conditioned to transmit a succession of 8 MHz bursts of sonic energy into the adjacent wrist tissue.

In use, the transmitted bursts of sonic energy are scattered by red blood cells flowing through the subject's radial artery 680, and a portion of the scattered energy is directed back toward the ultrasonic transducer 604. The time required for the return energy to reach the ultrasonic transducer varies according to the speed of sound in the tissue and according to the depth of the artery. Typical transit times are in the range of 6 to 7 microseconds.

The ultrasonic transducer 604 is used to receive the reflected ultrasound energy during the dead times between the successive transmitted bursts. For the applanation application, the ultrasonic transducer therefore produces a received signal, of relatively low magnitude, and this received signal is coupled to an RF amplifier 681 for amplification. The amplified signal is then supplied to an RF switch 682, which gates the signal to the RF mixer 683 only during the dead times between successive transmitted bursts. The RF mixer 683 mixes these gated bursts with the original 8 MHz signal received from the oscillator.

The frequency of the ultrasonic transducer's transmit signal will differ from that of the return signal, because the scattering red blood cells within the radial artery are moving. Thus, the return signal, effectively, is frequency modulated by the blood flow velocity. The signal output by the RF mixer 683, therefore, will incorporate the 8 MHz fundamental frequency, as well as sum and difference frequencies of the transmit and return signals. This output signal is supplied to a lowpass filter 684 with cutoff frequency of 1 MHz, for removal of the 8 MHz fundamental frequency, as well as any higher-order harmonics from the difference frequencies. A bandpass filter 685 that ranges from 300 Hz to 4 KHz then removes all signal components other than those components representing the actual blood velocity.

The signal output from the bandpass filter 685 is supplied to a zero-axis crossing detector 687, which functions to produce a pulse each time the signal crosses a zero axis. These pulses are supplied to a frequency-to-voltage converter circuit 688, which produces a DC output signal indicative of the mean Doppler frequencies. The signal output by the bandpass filter 685 is also supplied to an audio amplifier 690, and in turn to a speaker 691, to enable an operator to hear a representation of the Doppler signals and thereby to determine when the transducer is located approximately over the radial artery.

The output of the gate logic circuit is also amplified via an amplifier 694, and when transverse positioning is desired, switched to the ultrasonic transducer 604. The received echoes are coupled to an RF amplifier 696 and output for further processing to determine minimum echo value as a function of position.

It is noted that while the embodiment of FIGS. 5a and 7 utilizes a preselected pulse duration of 8 microseconds and pulse repetition interval of 16 microseconds, other acoustic sampling techniques may be used in conjunction with the invention. For example, in a second embodiment of the ultrasonic driver and receiver circuit (not shown), the acoustic pulses are range-gated with a more complex implementation of the gate logic. As is well known in the signal processing arts, range-gating is a technique by which the pulse-to-pulse interval is varied based on the receipt of range information from earlier emitted and reflected pulses. Using this technique, the system may be "tuned" to receive echoes falling within a specific temporal window which is chosen based on the range of the echo-producing entity in relation to the acoustic source. The delay time before the gate is turned on determines the depth of the sample volume. The amount of time the gate is activated establishes the axial length of the sample volume. Thus, as the acoustic source (in this case the ultrasonic transducer 604) is tuned to the echo-producing entity (red blood cells, or arterial walls), the pulse repetition interval is shortened such that the system may obtain more samples per unit time, thereby increasing its resolution. It will be recognized that other acoustic processing techniques may also be used, all of which are considered to fall within the scope of the claims appended hereto.

Figure 8:
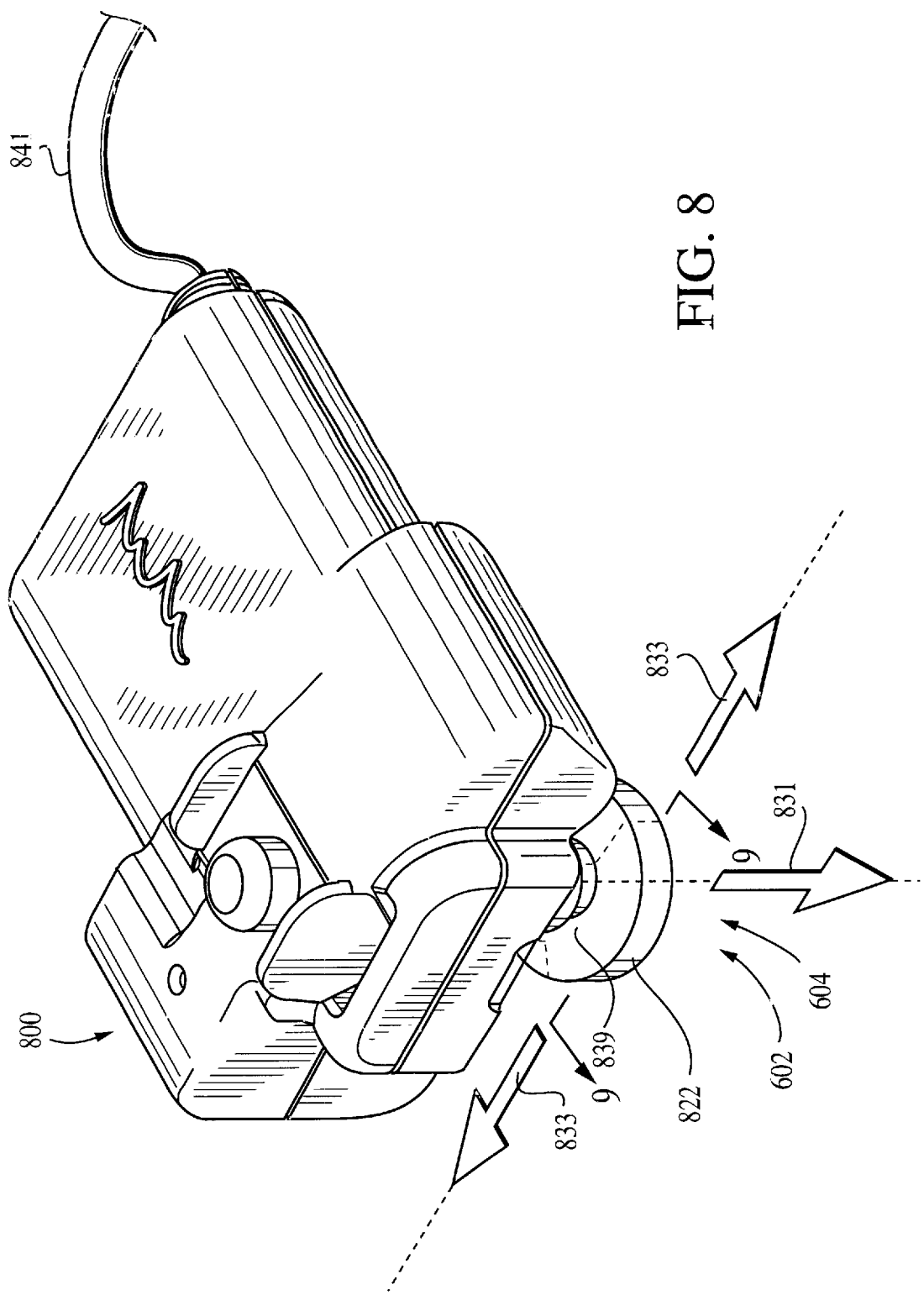
FIG. 8 is a perspective view of one embodiment of the applanation and transverse positioning assembly of the invention.
Figure 9:
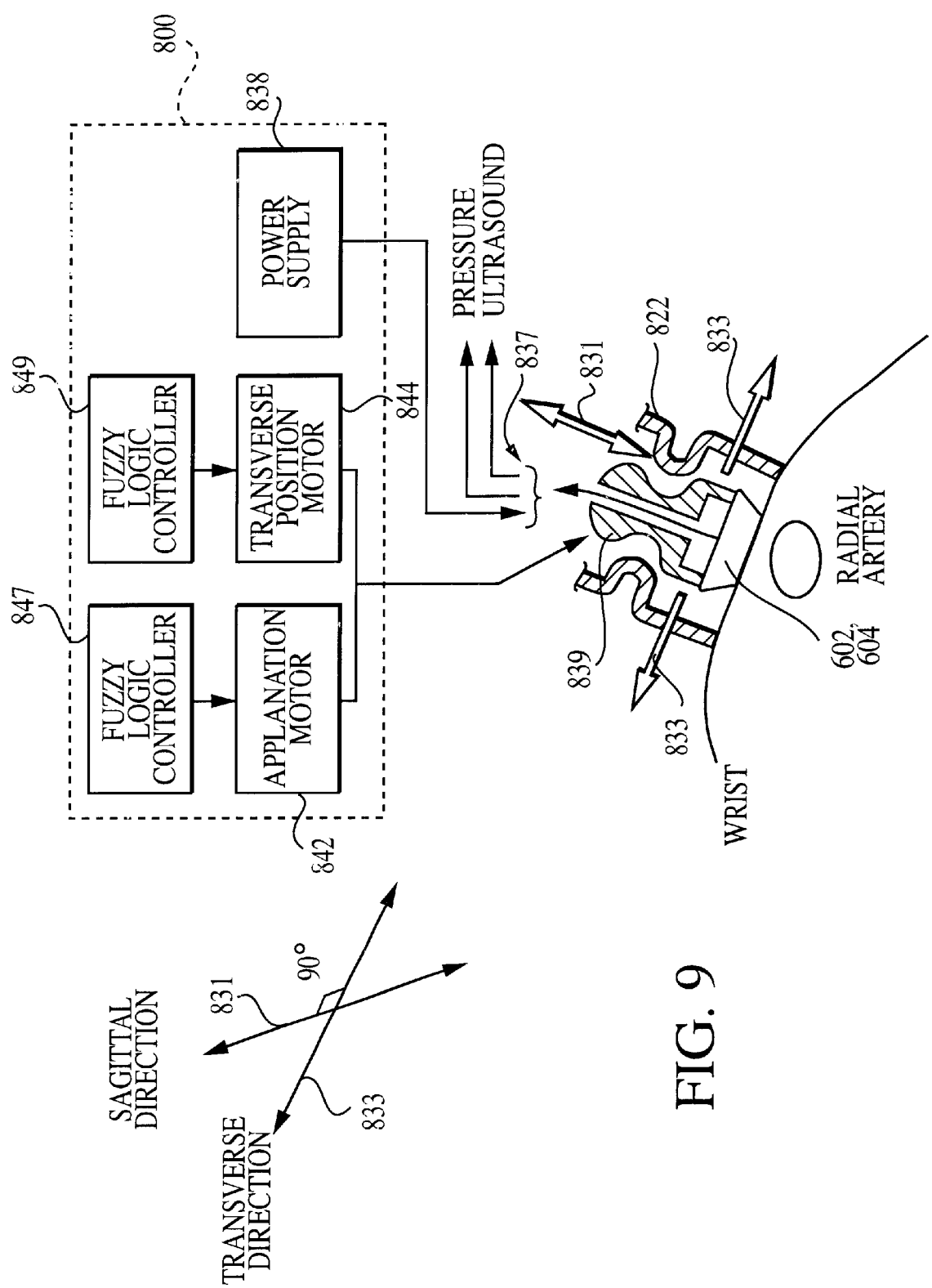
FIG. 9 is a cross-sectional view, including functional block diagram, of the blood pressure measurement system of the invention, taken along lines 9—9 of FIG. 8.

Referring now to FIGS. 8 and 9, one embodiment of the applanation and transverse positioning device 800 of the invention is illustrated. The device 800 is adapted to receive a transducer housing element 822 in the lower extensive portion 801 thereof. The transducer housing element contains the aforementioned pressure and ultrasonic transducers 602, 604 therein, the latter physically being combined into a single transducer element, although other configurations including a tandem ultrasonic/pressure configuration (not shown), or an array of multiple pressure and/or ultrasonic transducers, may be used. The transducers 602, 604 are free to move within the housing 822 in the sagittal direction 831 and the transverse direction 833 with respect to the artery, as driven by the applanation and positioning motors 842, 844. The housing element 822 of the present embodiment contacts the wrist skin circumferentially around the transducers 602, 604 which move with respect to the housing element 822 and the skin, although it will be appreciated that a variety of different configurations and methods may be used. For example, a substantially compliant housing which conforms to the tissue of the patient, yet allows the transducers 602, 604 to move in the desired directions within an aperture therein, may be substituted. When adhered to the wrist using the wrist brace disclosed herein in FIG. 10 (or other retaining mechanism), the active surface 810 of the transducers 602, 604 is in variable contact with the skin of the wrist, and roughly flush with the bottom edge of the housing element 822. The top of the transducers 602, 604 include an electrical connection 837 to the power supply 838 of the applanation and transverse positioning assembly 800, as well as to circuitry for processing the pressure and ultrasound signals from the transducers. The transducers are also coupled via a mechanical connection 839 to the motors of the applanation and transverse positioning assembly 800, such that the position of the transducers 602, 604 is varied in the sagittal and transverse directions by the applanation and transverse positioning motors 842, 844, respectively. While a ball-and-socket arrangement is illustrated for the mechanical connection 839 between the transducers 602, 604 and the motors, it will be appreciated that a variety of different arrangements (such as an articulated joint or sliding coupling) may be used. Collectively, the housing element 822 and the applanation and transverse positioning assembly 800 comprise a coupling device, which maintains the transducers 602, 604 properly coupled to the subject's wrist when mounted in the wrist brace of FIG. 10. The transducers 602, 604 move in the sagittal direction 831 within the housing element 822 as urged by the applanation motor 842 so as to compress the radial artery to varying degrees during blood pressure measurement. The transverse positioning motor 844 moves the transducers in the transverse direction 833 within the housing element 822 during transverse positioning (described below). In the present embodiment, the applanation motor is controlled by a fizzy logic control circuit 847 of the type well known in the art so as to perform applanation sweeps, which vary the degree of arterial compression, although other control schemes may be used. For example, the applanation of the artery may be performed so as to maintain the transmural pressure at or near zero. Alternatively, the applanation motor may be modulated by the control circuit in a periodic or continuous fashion such that the artery is compressed according to a desired profile, such as a sinusoid. Such control and modulation schemes are described in Applicant's two co-pending U.S. patent applications, Ser. Nos. 09/120,069 and 09/120,205, both entitled "Apparatus and Method for Non-Invasively Monitoring a Subject's Arterial Blood Pressure" and filed Jul. 20, 1998, which are incorporated herein by reference in their entirety.

The transverse positioning motor 844 of the assembly 800 is used to position the transducers 602, 604 directly over the artery of interest. Specifically, the ultrasonic emissions of the ultrasonic transducer 604 are substantially normal to the surface of the subject's skin and are used to generate echoes, which are reflected from the blood and tissues. These echoes are received by the transducer 604 and analyzed so as to determine their amplitude as a function of transverse position of the transducer over the artery. As with the applanation motor 842 described above, the transverse positioning motor 844 is controlled via a fuzzy logic control circuit 849 which signals the motor 844 to adjust the transverse position of the transducer such that the amplitude of the echoes (and SNR) is optimized. Alternatively, the user may manually position the transducer 604 using manual control circuitry based on an indication of the relative strength of the blood velocity echoes, such as may be provided to the user by an audible or visual representation thereof. For example, the audio output of the speaker 691 (FIG. 7), whose frequency is proportional to the amplitude of the received echoes, may be used to position the transducer 604. Many such control schemes for the transverse positioning motor are possible, all being within the scope of the claims appended hereto.

Figure 10:
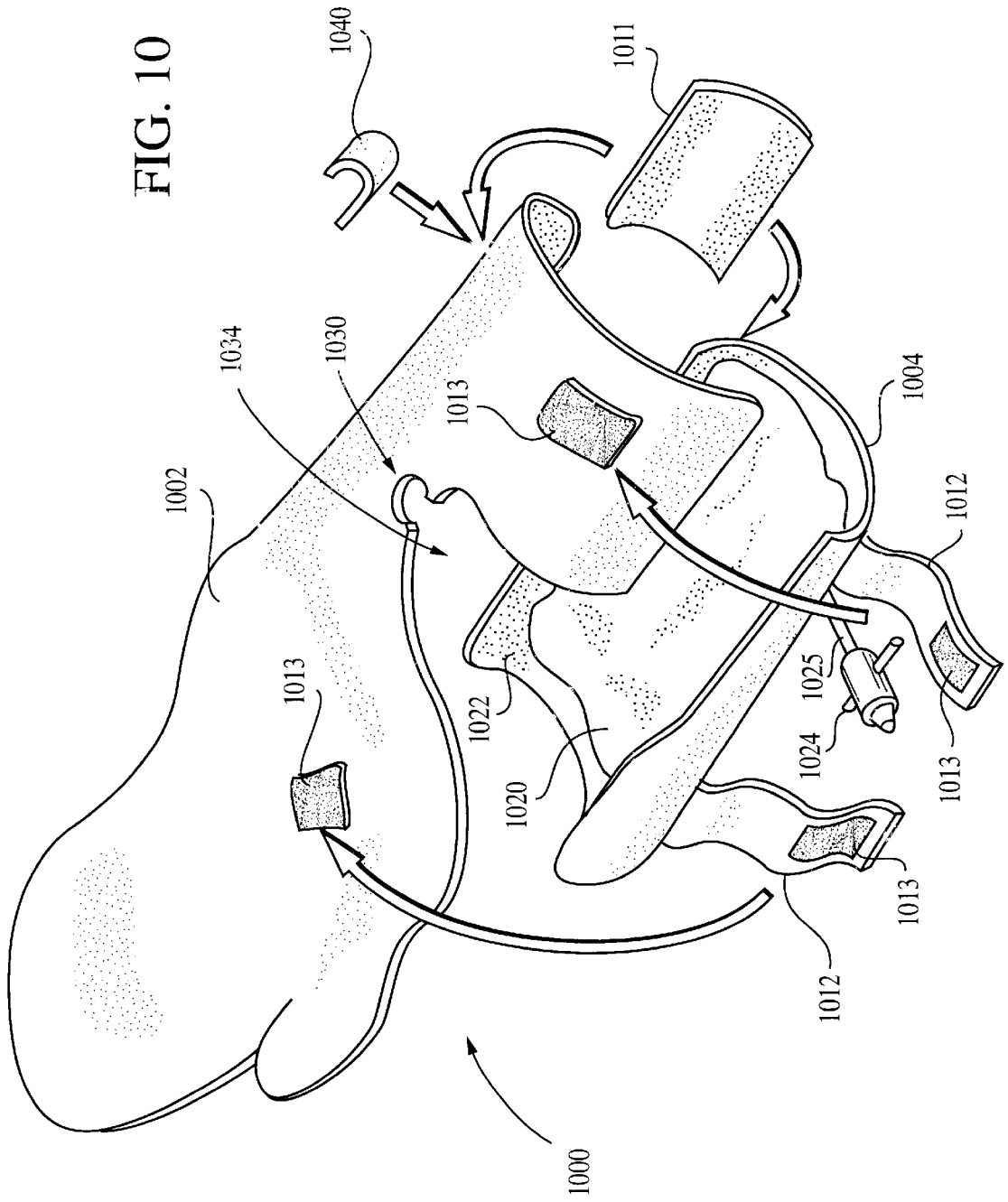
FIG. 10 is an exploded perspective view of one embodiment of the wrist brace of the present invention.
Figure 11:
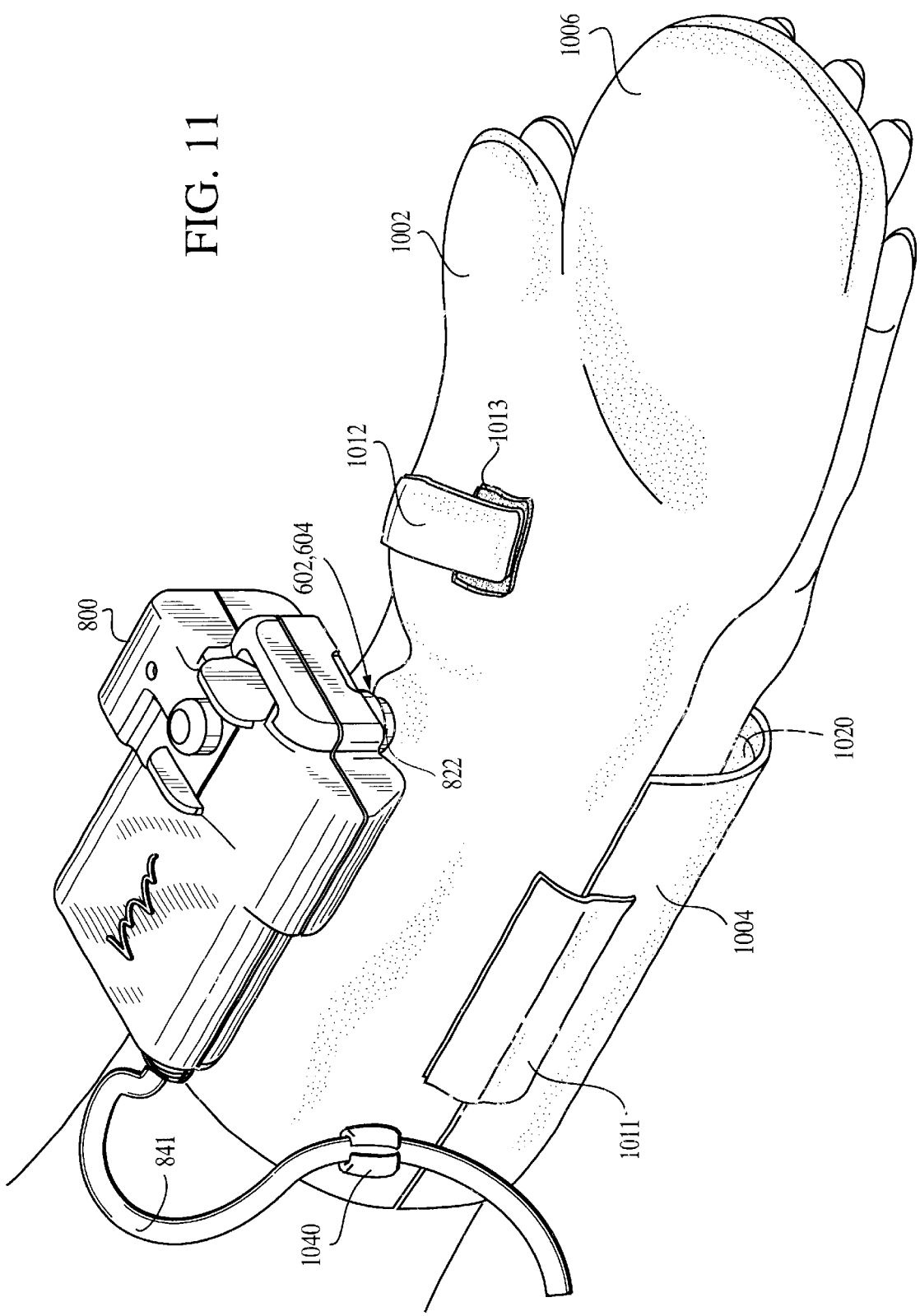
FIG. 11 is a perspective view of the wrist brace of FIG. 10 shown fitted to the wrist of a subject, and having the applanation and positioning assembly of FIG. 8 mounted thereon.

Referring now to FIGS. 10 and 11, the wrist brace 1000 of the invention is now described. In the embodiment of FIG. 10, the brace 1000 comprises an upper brace element 1002 and lower brace element 1004, which are adapted to fit the inner and outer wrist surfaces of the subject, respectively. As used herein, the terms "upper" and "lower" and "inner" and "outer" are merely descriptive of the orientation of the brace elements 1002, 1004 as illustrated in FIG. 10, and are in no way limiting as to the position or use of the brace. The upper brace element 1002 includes an extending portion 1006, which receives the inner surfaces of the subject's hand, as best shown in FIG. 11. The extending portion 1006 is contoured such that the subject's hand is retained in a natural, relaxed position, thereby increasing the time that the brace 1000 may be worn without discomfort. The upper and lower elements 1002, 1004 are joined on one common edge by a flexible fabric or polymer hinge 1011 which is fastened to both elements 1002, 1004. One or more straps 1012 are also fitted to the upper and lower elements 1002, 1004 such that when the brace 1000 is fitted to the subject's wrist and hand, the straps 1012 permit the upper and lower elements to be secured together firmly. In the present embodiment, the straps 1012 include fasteners 1013 such as Velcro tabs, although other arrangements such as mechanical clasps, snaps, slings, adhesives, or the like may be used. Likewise, the straps 1012 may be replaced partially or entirely with clasps or other similar fastening devices. It will be recognized that literally any means of maintaining the upper brace element 1002 in a substantially fixed position with respect to the lower brace element 1004 may be substituted for the straps 1012 showing FIGS. 10 and 11.

The upper and lower brace elements 1002, 1004 are advantageously formed using a partially flexible polymer material, thereby allowing for low manufacturing cost, excellent ruggedness, and some degree of compliance with the shape of the subject's tissue. Note, however, that sufficient rigidity of these components is required to accommodate the reaction forces generated by the applanation and transverse positioning assembly 800 shown in FIG. 8 above. Specifically, the applanation and transverse positioning assembly 800 is rigidly mounted to the upper brace element 1002, as shown in FIG. 11. In one embodiment, the housing element 822 fits within an opening 1034 formed within the upper brace element 1002 adjacent to the recess 1030 such that the assembly 800 can be easily placed and "snapped into" wrist brace 1000. In a first alternative embodiment (not shown), the housing element 822 is formed within the upper brace element 1002 such that the transducers 602, 604 fit within a central aperture formed within the element 822, and the applanation and positioning assembly 800 snaps on to the outer portion of the upper brace element 1002 directly above the transducer housing element 822. In a second alternative embodiment (not shown), the applanation and positioning assembly 800 is formed directly within the upper brace element 1002. In a third alternative embodiment (also not shown), the transducer elements 602, 604 and housing element 822 are disposed within the brace 1000, with the applanation and transverse positioning assembly 800 being removably mounted thereon. It will be recognized that many other alternative configurations are possible.

The electrical cabling 841 associated with the assembly 800 is also optionally received within a routing clip 1040 mounted on the exterior of the upper brace element 1002, thereby reducing the mechanical stress on the rigid mount 846 from the cabling 841 to some degree.

The lower brace element 1004 of the present embodiment also optionally includes an inflatable bladder 1020, which is received within and fastened to the interior surface 1022 of the lower brace element 1004. The bladder 1020 is formed of a flexible material (such as a plastic or rubber) so that it can comply with the shape of the subject's wrist, and accommodate varying degrees of inflation. As used herein, the term "inflation" is meant to include inflation of the bladder 1020 by gaseous and/or liquid substances. The bladder 1020 includes a stopcock 1024 and tube 1025, which allow the user to adjust the inflation of the bladder 1020 when required. The bladder may also be connected to an automatic inflation regulating system (not shown), which dynamically adjusts the inflation of the bladder 1020 to maintain optimal positioning and/or comfort for the subject. Alternatively, the bladder 1020 may be replaced by a substantially compliant pad (not shown), such as one made of foam rubber, which will at least partially adapt its shape to that of the subject's wrist, yet maintain the wrist firmly within the brace. It can be appreciated that many such alternative embodiments are possible.

Referring again to FIG. 11, the installation and positioning of the embodiment of FIGS. 8–10 is described. The wrist brace 1000 is first fitted to the arm of the subject by the clinician such that the opening 1034 and recess 1030 in the upper brace element 1002 are located roughly atop the pulse and the radial artery. The bladder 1020 is adjusted as needed to firmly maintain the position of the brace 1000. Next, the applanation and transverse positioning assembly 800 is snapped into the recess 1030, retaining it in position. The clinician verifies that the bottom of the housing element 822 is touching the skin of the patient's wrist, and is oriented roughly normal to the wrist tissue. The electrical cabling 841 is snapped into the routing clip 1040 as well. Lastly, the ultrasonic transducer (not shown) is energized and a signal applied thereto such that acoustic waves are transmitted into the artery and surrounding tissue; echoes resulting from reflection of these waves off of the blood velocity are used (as previously described) to drive the transverse positioning control circuit and motor so as to optimize the placement of the transducer over the artery. Applanation sweeps of the artery may then be conducted, as described with respect to FIG. 3a herein.

While the above detailed description has shown, described, and pointed out the fundamental novel features of the invention as applied to various embodiments, it will be understood that various omissions, substitutions, and changes in the form and details of the apparatus and methods illustrated may be made by those skilled in the art without departing from the spirit of the invention.

APPENDIX A

Algorithm Experiments

To demonstrate the maximum time-frequency principle, 10 learning data files were selected from past applanation sweeps that possessed high quality ultrasound, overcompression, and generally large mean arterial pressure (MAP) difference. MAP difference was calculated by comparing estimated MAP to the average of two cuff MAPs measured immediately before and after an applanation sweep. Two additional files were acquired with an additional constraint of sweeping down to a minimum diastolic value less than 30 mm Hg below the true diastole (specifically files 11 and 12). The data files were acquired using a variety of sensor geometries, position angles (steel mount angles are varied and unknown), and subjects, as illustrated in Table 1.

TABLE 1

Learning Data

| File | Subject | Sensor | Sensor Position | Mean Cuff Avg. Pressure (mm hg) | Arterial Max Pulsatile Estimate (mm Hg) | Time-Frequency Estimate (mm Hg) |
|---|---|---|---|---|---|---|
| 1 | 1 | mo30 | steel mount | 108 | 122 | 103 |
| 2 | 2 | mo30 | steel mount | 88 | 90 | 82 |
| 3 | 3 | mo30 | steel mount | 68 | 85 | 84 |
| 4 | 4 | mo30 | steel mount | 88 | 83 | 83 |
| 5 | 4 | dc22 | 0° pitch, 0° roll | 85 | 90 | 86 |
| 6 | 5 | dc22 | −10° pitch, +10° roll | 63 | 51 | 58 |
| 7 | 2 | dc22 | −10° pitch, −10° roll | 84 | 90 | 92 |
| 8 | 6 | dc29 | 0° pitch, 0° roll | 77 | 104 | 105 |
| 9 | 7 | dc29 | +10° pitch, −10° roll | 88 | 107 | 81 |
| 10 | 8 | mo30 | steel mount | 98 | 135 | 105 |
| 11 | 6 | dc33 | 0° pitch, 0° roll | 82 | 124 | 87 |
| 12 | 3 | dc19 | 0° pitch, 0° roll | 73 | 102 | 71 |
| | | | MAP error (mm Hg): | | 15 ± 17 | 3 ± 11 |

In each file, MAP was estimated by searching for the maximal pulsatile pressure. MAP was also estimated by determining the MAP associated with a pressure waveform with the maximal mean time-frequency distribution. The Pseudo Wigner distribution of the velocity, with k=0, calculated. Within each pressure waveform time interval, the mean distribution value was then calculated. The algorithm for calculating the maximal time-frequency distribution was "tuned" to the 12 files. By tuning, secondary algorithm steps such as the determination of the choice of the first pressure and velocity waveforms to be analyzed within a sweep were optimized. Also, the MAP differences using the maximum mean distribution versus maximum diastolic distribution were evaluated. While the results from both methods were insignificantly different, the maximum mean distribution was easier to calculate.

Once the mean time-frequency algorithm was tuned, the MAP in 6 new data files (again, with various sensor geometries, position angles, and subjects; see Table 2) was estimated and compared to the cuff MAP. For each comparison, the mean and standard deviation of the MAP difference was calculated. The paired, two-sided t test was used to assess significant differences between methods, using a 95% confidence interval.

TABLE 2

Testing Data

| File | Subject | Sensor | Sensor Position | Mean Cuff Avg. Pressure (mm hg) | Arterial Max Pulsatile Estimate (mm Hg) | Time-Frequency Estimate (mm Hg) |
|---|---|---|---|---|---|---|
| 13 | 9 | mo30 | steel mount | 73 | 93 | 73 |
| 14 | 4 | dc18 | 0° pitch, 0° roll | 79 | 97 | 89 |

TABLE 2-continued

Testing Data

| File | Subject | Sensor | Sensor Position | Mean Cuff Avg. Pressure (mm hg) | Arterial Max Pulsatile Estimate (mm Hg) | Time-Frequency Estimate (mm Hg) |
|---|---|---|---|---|---|---|
| 15 | 8 | mo30 | steel mount | 88 | 114 | 95 |
| 16 | 2 | mo30 | steel mount | 88 | 101 | 85 |
| 17 | 5 | dc22 | +10° pitch, −10° roll | 64 | 60 | 64 |
| 18 | 2 | dc33 | +10° pitch, −10° roll | 79 | 120 | 85 |
| | | | MAP error (mm Hg): | | 19 ± 15 | 3 ± 5 |

Results

For the learning data (Table 1), the maximum pulsatile MAP difference was 15±17 mm Hg; the maximum time-frequency MAP difference was 3±11 mm Hg. For the testing data (Table 2), the maximum pulsatile MAP difference was 19±15 mm Hg; the maximum time-frequency MAP difference was 3±5 mm Hg. In both the learning and testing data sets, the results obtained from the maximum time-frequency method were significantly different from those obtained using the maximum pulsatile method ($p \leq 0.02$ and $p \leq 0.03$, respectively).

What is claimed is:

1. A method of measuring blood pressure within a blood vessel of a subject, comprising:

compressing at least a portion of said blood vessel to a varying degree as a function of time;

transmitting an acoustic wave into said blood vessel during said compressing;

receiving an echo of said acoustic wave from said blood vessel during said compressing;

estimating at least one parameter based on said echo; and determining the pressure within said blood vessel when said parameter is estimated to satisfy a predetermined condition.

2. The method of claim 1, further comprising:

measuring the frequency of said echo; and calculating the velocity of blood flowing within said blood vessel as a function of the measured frequency.

3. The method of claim 2, wherein the act of estimating at least one parameter comprises estimating the diameter of said blood vessel.

4. The method of claim 1, wherein the act of compressing comprises compressing the radial artery of human being.

5. The method of claim 1, further comprising:

selecting at least one time interval; and calculating a mean distribution value during said at least one time interval.

6. The method of claim 5, herein said time-frequency distribution comprises a pseudo-Wigner distribution.

7. The method of claim 1, herein said predetermined condition comprises a maximized time-frequency distribution.

8. The method of claim 1, further comprising varying the position of transducers which transmit said acoustic wave and receive said echo, respectively, in relation to said blood vessel and based on said echo.

9. The method of claim 8, wherein the act of varying the position comprises varying the transverse position of transducers which transmit said acoustic wave and receive said echo, respectively, in relation to said blood vessel and based at least in part on the amplitude of said echo.

10. A method of measuring blood pressure, comprising:

positioning a first transducer capable of producing a first signal related to the pressure applied thereto, in proximity to the blood vessel of a subject;

urging said first transducer against the tissue of said subject, said first transducer at least partly compressing said blood vessel in response to said urging;

positioning a second transducer capable or transmitting and receiving acoustic energy in proximity to said blood vessel;

transmitting an acoustic wave into said blood vessel using said second transducer;

receiving at least one echo from said blood vessel using said second transducer, said second transducer generating a second signal related to said echo;

measuring the frequency of said echo based on said second signal;

forming a time-frequency distribution based on said frequency; and measuring the pressure within said blood vessel using said first transducer when said time-frequency distribution is maximized.

11. A method of measuring blood pressure within a blood vessel of a subject, comprising:

progressively varying the compression of at least a portion of said blood vessel;

transmitting acoustic energy into said blood vessel during at least a portion of said act of varying the compression;

receiving echoes of said acoustic energy from said blood vessel during at least a portion of said act of varying the compression;

forming a time-frequency representation of said echoes; and determining the pressure within said blood vessel when said representation satisfies a given condition.

12. The method of claim 11, wherein said act of progressively varying the compression comprises:

compressing said blood vessel to a substantially occluded state; and reducing the level of compression of said blood vessel thereafter.

13. The method of claim 11, wherein said act of transmitting comprises:

positioning a transducer element substantially adjacent said blood vessel and in contact with the skin superior thereto; and transmitting ultrasonic waves into said blood vessel.

14. The method of claim 11, wherein said act of forming a time-frequency representation comprises forming a time frequency distribution, and said act of determining comprises determining the pressure when said time-frequency distribution is substantially maximized.

15. The method of claim 14, wherein said time frequency distribution comprises a Wigner distribution.

16. The method of claim 14, further comprising:

selecting at least one time interval; and calculating a mean value of said distribution during said at least one time interval.

17. The method of claim 11, wherein said time frequency representation comprises a Wigner distribution.

18. The method of claim 11, further comprising:

selecting at least one time interval; and calculating a mean value of said representation during said at least one time interval.

19. The method of claim 11, further comprising varying the position of the source of said acoustic energy with respect to said blood vessel based at least in part on said received echoes.

20. The method of claim 19, wherein said act of varying the position comprises varying the position based at least in part on the amplitude of said echoes.

21. The method of claim 11, wherein said act of varying the compression comprises compressing a portion of said blood vessel using a surface of a tonometric pressure transducer.

22. The method of claim 11, wherein said act of forming a time-frequency representation comprises determining the mean time-frequency distribution at zero (0) Hz.

23. The method of claim 11, wherein said act of forming a time-frequency representation comprises:
  determining the blood velocity;
  forming a time-frequency distribution based at least in part on said blood velocity; and
  calculating the mean distribution value for each cardiac beat of said subject.

24. A method of measuring blood pressure within a blood vessel of a subject, comprising the steps of:
  progressively varying the compression of at least a portion of said blood vessel to alter the hemodynamic properties thereof;
  transmitting acoustic energy into said blood vessel during at least a portion of said act of varying the compression to generate echoes form said vessel and blood contained therein;
  receiving said echoes of said acoustic energy from said blood vessel during at least a portion of said act of varying the compression;
  forming a time-frequency representation of said echoes to identify at least one predetermined condition therein; and
  determining when said representation satisfies said predetermined condition to determine the pressure within said blood vessel non-invasively.

25. A method of measuring blood pressure within the radial artery of a living subject, comprising:
  varying the level of compression of at least a portion of said artery;
  transmitting ultrasonic energy into said artery during at least a portion of said act of varying the compression;
  receiving echoes of said acoustic energy from said artery during at least a portion of said act of varying the compression;
  determining blood velocity based at least in part on said echoes;
  forming a time-frequency distribution of said echoes based at least in part on said blood velocity;
  selecting an interval within which said distribution is evaluated;
  determining the mean of said distribution within said interval; and
  determining the pressure within said artery when said mean of said distribution satisfies a given condition.

26. A blood pressure monitoring device, comprising:
  first apparatus adapted to compress a blood vessel of a subject and measure the pressure applied thereto;
  second apparatus adapted to transmit acoustic energy into said blood vessel and receive at least one echo resulting therefrom; and
  a processor operatively coupled to said first and second apparatus and configured to process said measured pressure and said at least one echo;
  wherein said device is further configured to:
    (i) progressively vary the compression of at least a portion of said blood vessel;
    (ii) transmit said acoustic energy into said blood vessel and receive said at least one echo therefrom during at least a portion of said act of varying the compression;
    (iii) form a time-frequency representation of said at least one echo using at least said processor; and
    (iv) determine the pressure within said blood vessel when said representation satisfies a given condition.

* * * * *

UNITED STATES PATENT AND TRADEMARK OFFICE
CERTIFICATE OF CORRECTION

PATENT NO.    : 6,471,655 B1
DATED         : October 29, 2002
INVENTOR(S)   : Gail D. Baura It is certified that error appears in the above-identified patent and that said Letters Patent is hereby corrected as shown below:

<u>Column 3,</u>
Lines 26-51,

"In a third aspect of the invention, an improved blood pressure monitoring device is disclosed. The device generally comprises: first apparatus adapted to compress a blood vessel of a subject and measure the pressure applied thereto; second apparatus adapted to transmit acoustic energy into the blood vessel and receive at least one echo resulting therefrom; and a processor operatively coupled to the first and second apparatus and configured to process the measured pressure and the at the compression of at least a portion of the blood vessel; (ii) transmit the acoustic energy into the blood vessel and receive the at least one echo therefrom during at least a portion of the act of varying the compression; (iii) form a time-frequency representation of the at least one echo using at least the processor; and (iv) determine the pressure within the blood vessel when the representation satisfies a given condition. In one exemplary embodiment, a pressure transducer and an ultrasonic transducer are contained within a common unit worn on the subject's wrist, and measure both the arterial applanation and arterial blood velocity. The time-frequency distribution is determined from the velocity data, as calculated by an algorithm running on a digital signal processor (DSP). The time at which the time-frequency distribution is maximized corresponds to the time at which the transmural pressure equals zero, and the mean pressure read by the pressure transducer equals the MAP."

Should Read:

--In a third aspect of the invention, an improved blood pressure monitoring device is disclosed. The device generally comprises: first apparatus adapted to compress a blood vessel of a subject and measure the pressure applied thereto; second apparatus adapted to transmit acoustic energy into the blood vessel and receive at least one echo resulting therefrom; and a processor operatively coupled to the first and second apparatus and configured to process the measured pressure and the at least one echo; wherein the device is further configured to: (i) progressively vary the compression of at least a portion of the blood vessel; (ii) transmit the acoustic energy into the blood vessel and receive the at least one echo therefrom during at least a portion of the act of varying the compression; (iii) form a time-frequency representation of the at least one echo using at least the processor; and (iv) determine the pressure within the blood vessel when the representation satisfies a given condition. In one exemplary embodiment, a pressure transducer and an ultrasonic transducer are contained within a common unit worn on the subject's wrist, and measure both the arterial applanation and arterial blood velocity. The time-frequency distribution is determined from the velocity data, as calculated by an algorithm running on a digital signal processor (DSP). The time at which the time-frequency distribution is maximized corresponds to the time at which the transmural pressure equals zero, and the mean pressure read by the pressure transducer equals the MAP.--

UNITED STATES PATENT AND TRADEMARK OFFICE
CERTIFICATE OF CORRECTION

PATENT NO.    : 6,471,655 B1
DATED         : October 29, 2002
INVENTOR(S)   : Gail D. Baura It is certified that error appears in the above-identified patent and that said Letters Patent is hereby corrected as shown below:

Column 17,
Line 38, "estimating at least one parameter based on said echo; and" should read
-- estimating at least one parameter based on said echo by forming a time-frequency distribution of said echo; and --
Lines 56-57, "The method of claim 5, herein said time-frequency distribution comprises a pseudo-Wigner distribution." should read
-- The method of claim 5, wherein said time-frequency distribution comprises a pseudo-Wigner distribution. --
Lines 58-60, "The method of claim 1, herein said predetermined condition comprises a maximized time-frequency distribution." should read
-- The method of claim 1, wherein said predetermined condition comprises a maximized time-frequency distribution. --

Signed and Sealed this

Twenty-ninth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,471,655 B1
DATED : October 29, 2002
INVENTOR(S) : Gail D. Baura

It is certified that error appears in the above-identified patent and that said Letters Patent is hereby corrected as shown below:

<u>Title page,</u>
Item [73], reads:
"[73]　Assignee:　VitalWave Corporation, San Diego, CA (US)"
should read:
-- [73]　Assignee:　Tensys Medical, Inc., San Diego, CA (US) --

Signed and Sealed this

Eleventh Day of November, 2003

JAMES E. ROGAN
*Director of the United States Patent and Trademark Office*